(12) United States Patent
Medcalf et al.

(10) Patent No.: US 8,071,091 B2
(45) Date of Patent: *Dec. 6, 2011

(54) NON-NEUROTOXIC PLASMINOGEN ACTIVATING FACTORS FOR TREATING STROKE

(75) Inventors: Robert Medcalf, Victoria (AU); Mariola Söhngen, Aachen (DE); Wolfgang Söhngen, Aachen (DE); Wolf-Dieter Schleuning, Berlin (DE)

(73) Assignee: Paion Deutschland GmbH, Aachen (DE)

( * ) Notice: Subject to any disclaimer, the term of this patent is extended or adjusted under 35 U.S.C. 154(b) by 362 days.

This patent is subject to a terminal disclaimer.

(21) Appl. No.: 12/163,828

(22) Filed: Jun. 27, 2008

(65) Prior Publication Data

US 2009/0004176 A1   Jan. 1, 2009

Related U.S. Application Data

(63) Continuation of application No. 11/311,475, filed on Dec. 20, 2005, now abandoned, which is a continuation of application No. 10/184,018, filed on Jun. 28, 2002, now abandoned.

(30) Foreign Application Priority Data

Nov. 2, 2001 (DE) .................................. 101 53 601
Dec. 17, 2001 (EP) ..................................... 01130006

(51) Int. Cl.
*A61K 38/48* (2006.01)
*C12N 9/64* (2006.01)
(52) U.S. Cl. ..................................... 424/94.64; 435/226
(58) Field of Classification Search ........................ None
See application file for complete search history.

(56) References Cited

U.S. PATENT DOCUMENTS

| | | | |
|---|---|---|---|
| 4,766,075 A | 8/1988 | Goeddel et al. | |
| 5,094,953 A | 3/1992 | Anderson et al. | |
| 5,223,256 A * | 6/1993 | Stern et al. | 424/94.63 |
| 5,244,806 A | 9/1993 | Bang et al. | |
| 5,314,818 A | 5/1994 | Anderson et al. | |
| 5,326,700 A | 7/1994 | Berg et al. | |
| 5,500,411 A | 3/1996 | Martin et al. | |
| 5,510,330 A | 4/1996 | Martin et al. | |
| 5,595,736 A | 1/1997 | Berg et al. | |
| 5,648,250 A | 7/1997 | Niwa et al. | |

(Continued)

FOREIGN PATENT DOCUMENTS

CA    5 524 573    11/2004

(Continued)

OTHER PUBLICATIONS

Mellott, M. J., et al., 1992, "Vampire bat salivary plasminogen activator promotes rapid and sustained reperfusion withour concomitatant systemic plasminogen activation in a canine model of arterial thrombosis", Arteriosclerosis and Thrombosis, vol. 12, No. 2 pp. 212-221.*

(Continued)

*Primary Examiner* — Manjunath Rao
*Assistant Examiner* — William W Moore
(74) *Attorney, Agent, or Firm* — Wilmer Cutler Pickering Hale and Dorr, LLP

(57) ABSTRACT

The invention pertains to the use and production of non-neurotoxic plasminogen activating factors e.g. of *Desmodus rotundus* (DSPA) for the therapeutic treatment of stroke in humans in order to provide a new therapeutic concept for treating stroke in humans.

6 Claims, 10 Drawing Sheets

Constant relative increase of t-PA Neurotoxicity is time limiting for therapy and "additive" to rt-PA Neurotoxicity

U.S. PATENT DOCUMENTS

| | | | |
|---|---|---|---|
| 5,676,947 | A | 10/1997 | Martin et al. |
| 5,714,145 | A | 2/1998 | Anderson et al. |
| 5,731,186 | A | 3/1998 | McCaman et al. |
| 5,741,771 | A | 4/1998 | Dawson et al. |
| 5,786,187 | A | 7/1998 | Strickland et al. |
| 5,827,832 | A | 10/1998 | Sandage et al. |
| 5,830,849 | A | 11/1998 | Dixon et al. |
| 5,876,971 | A * | 3/1999 | Noeske-Jungblut et al. 435/69.1 |
| 5,891,664 | A * | 4/1999 | Danø et al. .......... 435/69.1 |
| 5,945,432 | A | 8/1999 | Bednar et al. |
| 6,008,019 | A | 12/1999 | Baldus et al. |
| 6,235,278 | B1 | 5/2001 | Miller |
| 6,235,279 | B1 | 5/2001 | Martin et al. |
| 6,248,712 | B1 * | 6/2001 | Danø et al. .......... 514/2 |
| 2002/0081294 | A1 | 6/2002 | Bednar et al. |
| 2002/0098179 | A1 | 7/2002 | Brearley et al. |
| 2005/0048027 | A1 | 3/2005 | Söhngen et al. |
| 2006/0135425 | A1 | 6/2006 | Sohngen et al. |
| 2006/0142195 | A1 | 6/2006 | Medcalf et al. |
| 2008/0057050 | A1 | 3/2008 | Sohngen et al. |
| 2008/0213244 | A1 | 9/2008 | Sohngen |
| 2009/0004176 | A1 | 1/2009 | Medcalf et al. |
| 2009/0263373 | A1 | 10/2009 | Sohngen et al. |
| 2010/0272704 | A1 | 10/2010 | Sohngen et al. |

FOREIGN PATENT DOCUMENTS

| | | |
|---|---|---|
| DE | 39 04 580 | 8/1990 |
| DE | 39 17 949 A | 1/1991 |
| DE | 41 23 845 A | 1/1993 |
| DE | 689 16 532 T2 | 1/1995 |
| DE | 692 15 537 T | 4/1997 |
| DE | 692 15 537 T2 | 4/1997 |
| EP | 0 242 836 A1 | 10/1987 |
| EP | 0 273 774 A2 | 7/1988 |
| EP | 0 352 119 | 1/1990 |
| EP | 0 352 710 A2 | 1/1990 |
| EP | 0 383 417 B1 | 8/1990 |
| EP | 0 386 240 A1 | 9/1990 |
| EP | 0 618 973 B1 | 10/1994 |
| EP | 0 093 619 | 9/1996 |
| EP | 1 308 166 | 5/2003 |
| JP | 6506459 | 7/1994 |
| WO | WO 89/09266 | 10/1989 |
| WO | WO 91/05048 | 4/1991 |
| WO | WO 93/12238 | 6/1993 |
| WO | WO 96/01312 | 1/1996 |
| WO | WO 97/29188 | 8/1998 |
| WO | WO 01/51613 | 7/2001 |
| WO | WO 01/51614 | 7/2001 |
| WO | WO 03/037363 A2 | 5/2003 |
| WO | WO 03/037363 T | 5/2003 |
| WO | WO 2004/096267 | 11/2004 |
| WO | WO 2004/096268 A3 | 11/2004 |
| WO | WO 2004/098635 | 11/2004 |
| WO | WO-2005/018564 | 3/2005 |
| WO | WO 2005/026341 | 3/2005 |

OTHER PUBLICATIONS

Abstract of DE 39 04 580, published Aug. 16, 1990.
Abstract of EP 1 308 166, published May 7, 2003.
Abstract of WO 04/096267, published Nov. 11, 2004.
Abstract of WO 04/098635, published Nov. 18, 2004.
Abstract of EP 0 242 836, published Oct. 28, 1987.
Adams, H. P., et al., "Guidelines for thrombolytic therapy for acute stroke: a supplement to the guidelines for the management of patients with acute ischemic stroke, a statement for healthcare professionals from a special writing group of the stroke council, American Heart Association," Circulation, 94(5):1167-1174 (1996).
Adams, H. P., et al., "Guidelines for the early management of patients with ischemic stroke: a scientific statement from the stroke council of the American stroke association," Stroke, 34:1056-1083 (2003).
Albers, G. W., et al., "Antithrombotic and thrombolytic therapy for ischemic stroke: American college of chest physicians evidence-based clinical practice guidelines (8th edition)," Chest, 133:630S-669S (2008).
Albers, G. W., et al., "Desmoteplase 3-9 hours after acute ischemic stroke: an update on the DIAS clinical trial program," Poster at the International Stroke Conference, Feb. 24, 2010.
Alkawi, A., et al., "Advances in thrombolytics and mechanical devices for treatment of acute ischemic stroke," Neurological Research, 27(1):542-549 (2005).
Asplund, K., et al., "How do stroke units improve patients outcomes? a collaborative systematic review of the randomized trials," Stroke, 28(11):2139-2144 (1997).
Atalaya, J. L., et al., "Neurotransmitters and receptors," Journal of Cerebral Blood Flow & Metabolism, 25:S578 (2005).
Bath, Philip, "Alteplase not yet proven for acute ischaemic stroke," The Lancet, 352:1238-1239 (1998).
Bhana, N., et al., "Lanoteplase," Biodrugs, 13(3):217-224 (2000).
Bondaryk, et al., "Microheterogeneity, standardization and characterization in glycoprotein drugs," Curr. Drug Discov., 4:31-32 (2004).
Broderick, J.P. et al., "Treatment of acute ischemic stroke: part I: recanalization strategies," Circulation, 106:1563-1569 (2002).
Brott, T. et al., "Treatment of acute ischemic stroke," The New Engl. J. Med., 343(10):710-722 (2000).
Clark, W. M., et al, "The rtPA (Alteplase) 0- to 6-hour acute stroke trial, part A (A 0276g) : results of a double-blind, placebo-controlled, multicenter study," Stroke, 31:811-816 (2002).
Collen, D., "Fibrin-selective thrombolytic therapy for acute myocardial infarction," Circulation, 93:857-865 (1996).
Colman, A., et al., "Post-translational modification of exogenous proteins in Xenopus laevis oocytes," Biochemical Society Transactions, 12:932-937 (1984).
Degen, S.J.F., et al., "The human tissue plasminogen activator gene," The Journal of Biological Chemistry, 261(15):6972-6985 (1986).
del Zoppo, G.J., et al., "Recombinant tissue plasminogen activator in acute thrombotic and embolic stroke," Ann Neurol, 32(1):78-86 (1992)—ABSTRACT.
DiMasi, J. A., et al., "The price of innovation: new estimates of drug development costs," Journal of Health Economics, 22:151-185 (2003).
Donnan, G. A., et al., "Stroke drug development usually, but not always, animal models," Stroke, 36:2326 (2005).
Epple, G. et al., "Prion protein stimulates tissue-type plasminogen activator-mediated plasmin generation via a lysine-binding site on kringle 2," Journal of Thrombosis and Haemostasis, 2:962-968 (2004).
Fisher, M., et al., "Recommendations for standards regarding preclinical neuroprotective and restorative drug development," Stroke, 30:2752-2758 (1999).
Fisher, M., "Use of animal models has not contributed to development of acute stroke therapies con," Stroke, 36:2324-2325 (2005).
Fisher, M., "Enhancing the development and approval of acute stroke therapies, stroke therapy academic industry roundtable," Stroke, 36:1808-1813 (2005).
Fisher, M., et al., "Emerging therapies for acute ischemic stroke new therapies on trial," Stroke, 34:359-361 (2003).
Fisher, M., "The ischemic penumbra: a new opportunity for neuroprotection," Cerebrovasc Dis, 21(2):64-70 (2006).
Furlan, A., et al., "Dose escalation of desmoteplase for acute ischemic stroke (DEDAS): evidence of safety and efficacy 3 to 9 hours after stroke onset," Stroke, 37:1227-1231 (2006).
Furlan, A., et al., "Intra-arterial prourokinase for acute ischemic stroke: the PROACT II study: a randomized controlled trial," JAMA, 282(21):2003-2011 (1999).
"GISSI-2: a factorial randomized trial of alteplase versus streptokinase and heparin versus no heparin among 12,490 patients with acute myocardial infarction. Gruppo italiano per lo studio della sopravvivenza nell'Infarto miocardico," Lancet, 336(8707):65-71 (1990)—Abstract.
Grandjean, C. et al., "Vampire bats yield potent clot buster for ischemic stroke," Journal of Cardiovascular Nursing, 19(6):417-420 (2004).
Grotta, J. C., et al., "Report of the stroke progress review group," National Institute of Neurological Disorders and Stroke, (2002).

Gusto Trial, "An international randomized trial comparing four thrombolytic strategies for acute myocardial infarction," The New England Journal of Medicine, 329(10):673-683 (1993).

Gusto III Study, "A comparison of reteplase with alteplase for acute myocardial infarction," The New England Journal of Medicine, 337(16):1118-1123 (1997).

Hacke, W., et al., "Intravenous desmoteplase in patients with acute ischaemic stroke selected by MRI perfusion-diffusion weighted imaging or perfusion CT (DIAS-2): a prospective, randomized, double-blind, placebo-controlled study," Lancet Neurol, 8:141-150 (2009).

Heymans, et al., "Outcome and one year follow-up of intra-arterial staphylokinase in 191 patients with peripheral arterial occlusion," Thromb. Haemost, 83:666-671 (2000).

International Search Report for PCT/EP2003/04729 dated Sep. 8, 2003.

Interview Summary dated Jan. 29, 2008, for U.S. Appl. No. 10/494,004.

Interview Summary dated Aug. 6, 2008, for U.S. Appl. No. 10/494,004.

Interview Summary dated Mar. 27, 2008, for U.S. Appl. No. 11/311,475.

Jiao, J. et al., "Characterization of a recombinant chimeric plasminogen activator with enhanced fibrin binding," Biochimica et Biophsica Acta, 1546:399-405 (2001).

Kase et al., Cerberal hemorrhage after intra-arterial thrombolysis for ischemic stroke, Neurology, Nov. 1 of 2, 57:1603-1610 (2001).

Kaste, M., "Thrombolysis in ischaemic stroke—present and future: role of combined therapy," Cerebrovasc. Dis., 11(Suppl. 1):55-59 (2001).

Kaste, M., "Use of animal models has not contributed to development of acute stroke therapies: Pro," Stroke, 36:2323-2324 (2005).

Lee, et al., "Local intraarterial urokinase thrombolysis of acute ischemic stroke with or without intravenous abciximab: a pilot study," J Vasc Inter Radio!, 13:769-773 (2002).

Lees, K. R., et al., "Time to treatment with intravenous alteplase and outcome in stroke: an updated pooled analysis of ECASS, ATLANTIS, NINDS, and EPITHET trials," Lancet, 375:1695-1703 (2010).

Leker, R. R., et al., "Novel therapies for acute ischemic stroke," IMAJ, 8:788-792 (2006).

Lopez-Atalaya, J.P., et al., "Recombinant desmodus rotundus salivary plasminogen activator crosses the blood-brain barrier through a low-density lipoprotein receptor-related protein-dependent mechanism without exerting neurotoxic effects," Stroke, 38:1036-1043 (2007).

Lopez-Yunez, A.M., et al., "Protocol violations in community-based rTPA stroke treatment are associated with symptomatic intracerebral hemorrhage," Stroke, 32:12-16 (2001).

Lo, E. H., et al., "Mechanisms, challenges and opportunities in stroke," Nature Reviews, Neuroscience, 4:399-415 (2003).

Marler, J. R., et al., "Early stroke treatment associated with better outcome: the NINDS tr-PA stroke study," Neurology, 55:1649-1655 (2000).

NINDS group, "Tissue plasminogen activator for acute ischemic stroke," National Institute of Neurological Disorders and Stroke rt-PA Study Group, New England Journal of Medicine, 333:1581-1587 (1995).

Nordt, et al., "Thrombolysis: newer thromolytic agents and their role in clinical medicine," Heart, 89:1358-1362 (2003).

Office Action in U.S. Appl. No. 10/184,018 dated Sep. 29, 2004.
Office Action in U.S. Appl. No. 10/184,018 dated Jun. 20, 2005.
Office Action in U.S. Appl. No. 10/184,018 dated Mar. 30, 2007.
Office Action in U.S. Appl. No. 10/571,560 dated Nov. 24, 2009.
Office Action in U.S. Appl. No. 10/571,560 dated Aug. 3, 2010.
Office Action in U.S. Appl. No. 10/555,583 dated Feb. 24, 2009.
Office Action in U.S. Appl. No. 10/555,583 dated Jul. 22, 2010.
Office Action in U.S. Appl. No. 11/878,686 dated Dec. 31, 2008.
Office Action in U.S. Appl. No. 11/878,686 dated Sep. 2, 2009.
Office Action in U.S. Appl. No. 11/878,686 dated Mar. 24, 2010.
Office Action in U.S. Appl. No. 11/878,686 dated Jul. 22, 2010.
Office Action in U.S. Appl. No. 12/196,785 dated Jan. 13, 2010.
Office Action (Interview Summary) in U.S. Appl. No. 12/196,785 dated Jul. 14, 2010.
Office Action in U.S. Appl. No. 12/196,785 dated Aug. 3, 2010.
Office Action in U.S. Appl. No. 11/311,475 dated Sep. 29, 2004.
Office Action in U.S. Appl. No. 11/311,475 dated Jun. 20, 2005.
Office Action in U.S. Appl. No. 11/311,475 dated Aug. 22, 2006.
Office Action in U.S. Appl. No. 11/311,475 dated May 31, 2007.
Office Action (Interview Summary) in U.S. Appl. No. 11/313,475 dated Mar. 27, 2008.

Peterson, K., "Thrombolytics a field in development," Riv. It. Neurobiologia, 53(1):7-14 (2007).

Read, S. J., "Pharmacological therapy for acute stroke," Curr. Opin. Invest. Drugs, 1(3):329-339 (2000).

Regenberg, A., et al., "The role of animal models in evaluating reasonable safety and efficacy for human trials of cell-based interventions for neurologic conditions," Journal of Cerebral Blood Flow & Metabolism, 29:1-9 (2009).

Ridker, P. M., et al., "Large-scale trials of thrombolytic therapy for acute myocardial infarction: GISSI-2, ISIS-3, and GUSTO-1," Annals of Internal Medicine, 119(6)530-532 (1993).

Semba, C.P., et al., "Alteplase as an alternative to urokinase," JVIR, 11:279-287 (2000).

Saver, J. L., et al., "Alteplase for ischaemic stroke—much sooner is much better," Lancet, 375:1667-1668 (2010).

Soehngen, M., et al., "Drugs for treatment of stroke," in Clinical trials of drugs and biopharmaceuticals, CRC, Lee, C., et al., eds. Ch. 15, 201-235 (2006).

Strbian, D., et al., "Ultraearly thrombolysis in acute ischemic stroke is associated with better outcome and lower mortality," Stroke, 41:712-716 (2010).

Stroke Unit Trialists' Collaboration, "How do stroke units improve patient outcomes?," Stroke, 28(11):2139-2144 (1997).

Sane, et al., Correlation between baseline plasminogen activator inhibitor levels and clinical outcome during therapy with tissue plasminogen activator for acute myocardial infarction, Thromb Haemost, 4:65(3)-275-279 (1991). Abstract.

Tanne, David et al., "Markers of increased risk of intracerebral hemorrhage after intravenous recombinant tissue plasminogen activator therapy for acute ischemic stroke in clinical practice: the multicenter rt-PA acute stroke survey," Circulation, 105:1679-1685 (2002).

Van de Werf, F., et al., "Single-bolus tenecteplase compared with front-loaded alteplase in acute myocardial infarction: the ASSENT-2 double-blind randomized trial," Lancet, 354:716-722 (1999).

van Zonneveld, A, et al, "Autonomous functions of structural domains on human tissue-type plasminogen activator," PNAS USA, 83:4670-4674 (1986).

Zhang, Z., et al., "Adjuvant treatment with neuroserpin increases the therapeutic window for tissue-type plasminogen activator administration in a rat model of embolic stroke," Circulation, 106:740-745 (2002).

Submission to the EPO in German dated Dec. 29, 2005 for European Application No. 01 130 006.8.

Rough English-language translation of Submission to the EPO in German dated Dec. 29, 2005 for European Application No. 01 130 006.8.

Declaration of Jeffrey I. Weitz under 37 C.F.R. § 1.132 filed in U.S. Appl. No. 12/196,785 on Jul. 13, 2010.

U.S. Appl. No. 10/184,018, filed Jun. 28, 2002, Medcalf R, et al.
U.S. Appl. No. 10/571,560, filed Mar. 10, 2006, Söhngen W, et al.

"4th International Symposium on Thrombolytic Therapy in Acute Ischemic Stroke" Cerebrovasc Dis. 6: 175-194 (1996).

"Bat Salvia Drug and New MRI Techniques Offer Hope for Acute Stroke Treatment" Neuro Infosource at www.neuroinfosource.com/news, posted Feb. 20, 2004.

"Randomised controlled trial of streptokinase, aspirin and combination of both in treatment of acute ischaemic stroke, Multicentre Acute Stroke Trial-Itlay (MAST-I)", Lancet, vol. 346, No. 8988, pp. 1509-1514 (1995).

"The International Stroke Trial (IST): a randomised trial of aspirin, subcutaneous heparin, both, or neither among 19 435 patients with acute ischaemic stroke", International Stroke Trial Collaborative Group, The Lancet 349: 1569-1581 (1997).

"Thrombolysis in Stroke not justified" SCRIP, No. 2265, p. 26 (1997).

"Thrombolytic Therapy with Streptokinase in Acute Ischemic Stroke, Multicentre Acute Stroke Trial-Europe Study Group", (MAST-E) The New Engl. J. Med. 335: 145-150 (1996).

"Thrombolytics: Therapeutic Class Review" A Pharmacy Healthcare Solutions/An AmerisourceBergen Company publication, ACPE No. 338-999-02-019-H01 (2002).

"Tissue plasminogen activator for acute ischemic stroke" National Institute of Neurological Disorders and stroke rt-PA study group. New. Engl. J. Med. 333: 1581-1587 (1995).

Adams H et al. "Design of the Trial of Org 10172 in Acute Stroke Treatment (TOAST)" Controlled Clinic Trials 18: 358-377 (1997).

Albers et al., Chest 119:300S 320S (2001).

Baird AE et al.; "Enlargement of human cerebral ischemic lesion volumes measured by diffusion-weighted magnetic resonance imaging" in Ann Neurol. 41:581-589 (1997).

Bakker AHF, et al.: The role of Lysil-Binding site of tissue . . . Journal of Biol. Chem. 270: 12355-12360 (1995).

Baldus B et al. "Thrombolysis of a cerbral clots with Desmodus salivary plasminogen activator alpha (ASPA alpha 1) compared to alteplase in a rabbit model of embolic stoke" Thromb. Harmostasis 73: 1398 (1995)—ABSTRACT.

Baranes D, Lederfein D, Huang YY, Chen M, Bailey CH, Kandel ER. Tissue plasminogen activator contributes to the late phase of LTP and to synaptic growth in the hippocampal mossy fiber pathway. Neuron 21:813-25 (1998).

Barnwell et al., "Safety and efficacy of delayed intraarterial urokinase therapy with mechanical clot disruption for thromboembolic stroke" Am J Neuroradiol 15:1817-1822 (1994)—ABSTRACT.

Bennett, W. "High Resolution Analysis of functional . . ." The Journal of Bio. Chem. vol. 266, No. 8, S. 5191-5201 (1991).

Bode and Renatus: "Tissue-type plasminogen activator: variants and crystal/solution structures . . . " Current Opinion in Structural Biology 7:865-872 (1997).

Bringmann P, Gruber D, Liese A, Toschi L, Kratzchmar J, Schleuning WD, Donner P. Structural features mediating fibrin selectivity of vampire bat plasminogen activators. J Biol Chem 270:25596-25603 (1995).

Butcher KS, et al.; "Refining the perfusion-diffusion mismatch hypothesis" Stroke 36: 1153-1159 (2005).

Callaway JK, Knight MJ, Watkins DJ, Beart PM, Jarrott B, Delaney PM. A novel, rapid, computerized method for quantitation of neuronal damage in a rat model of stroke. J Neurosci Methods 102:53-60 (2000).

Cannon CP, et al. "TNK-tissue plasminogen activators in myocardial infraction" Circulation 95:351-356 (1997).

Carmeliet P, Schoonjans L, Kieckens L, Ream B, Degen J, Bronson R, De Vos R, van den Oord JJ, Collen D, Mulligan RC. 1994. Physiological consequences of loss of plasminogen activator gene function in mice. Nature 368:419-424.

Cartwright T. The plasminogen activator of vampire bat saliva. Blood 43:317-326 (1974).

Chalela JA et al. "Early magnetic resonance imaging finding in patients receiving tissue plasminogen activator predict outcome" Insights into the pathophysiology of acute stroke in the thombolysis era. Ann. Neurol. 55: 105-112 (2004).

Chatterton JE et al. "Excitatory glycine receptors containing the NR3 family of NMDA receptor subunits" Nat. 415: 793-798 (2002)—ABSTRACT.

Chen ZL Strickland S. Neuronal death in the hippocampus is promoted by plasmin-catalysed degradation of laminin. Cell 91:917-925 (1997).

Chen, Z-L, Indyk, J.A., Bugge, T.H., Kombrinck, K.W., and Strickland S. Neuronal Death and blood-brain barrier breakdown after excitotoxic injury are independent processes. J. Neuroscience 19:9813-9820 (1999).

Choi, D., "Glutamate Neurotoxicity and Diseases of the Nervous System", Neuron, vol. 1, pp. 623-634 (1998).

Christou et al., "Timing of recanalization after tissue plasminogen activator therapy determined by transcranial doppler correlates with clinical recovery from ischemic stroke" Stroke 31:1812-1816 (2000).

Clark, W. M., et al.; "Recombinant tissue-type plasminogen activator (alterplase) for ischemic stroke 3 to 5 hours after symptom onset," JAMA, 282(21):2019-2026 (1999).

Das S et al. "Increased NMDA current and spine density in mice lacking the NMDA receptor subunit NR3A" Nature 393: 377-381 (1998)—Abstract.

Davidson et al., Biochem. J. 147(1):45 53 (1975)—Abstract.

Diller W, "Persistently Seeking Stroke Solution" in PAION Science News in Stroke 2003, pp. 7-17.

Docagne F et al. "Smad3-dependent induction of plasminogen activator inhibitor-1 in astrocytes mediates neuroprotective activity of transforming growth factor-beta1 against NMDA-induced necrosis" Mol. Cell. Neurosci. 21: 634-344—Abstract, (2002).

Donnan G et al. "Streptokinase for Acute Ischemic Stroke with Relationship to time of Administration" JAMA 267: 961-966 (1996).

Ellis V et al. "Plasminogen activation is stimulated by prion protein and regulated in a copper-dependent manner" Biochemistry 41:6891-6896 (2002).

Emeis, JJ et al. "Hepatic clearance of tissue-type plasminogen activator in rats" Thromb. Haemost. 54(3):661-664 (1985)—Abstract.

Fauber J "Salvia Drug may help fight strokes" in JSOnline—Milwaukee Journal Sentinel, Feb 6, 2004 edition.

Fischer M "Recommendations for Advancing Development of Acute Stroke Therapies; Stroke Therapy Academic Industry Roundtable 3" Stroke 34: 1539-1546 (2003).

Fischer M, et al.: Binding of disease-associated prion protein to plasminogen Nature 408: 479-483 (2000).

Frey U, Muller M, Kuhl D. A different form of long-lasting potentiation revealed in tissue plasminogen activator mutant mice. J Neurosci 16:2057-2063 (1996).

Furlan AJ "Acute Stroke therapy: Beyond IV tPa" Cleveland Clinic J. of Med 69: 730-734 (2002).

Gay, T. J., "UK Stroke researchers study new clot-busting drug," University of Kentucky Public Relations, (859)257-1754 (2003).

Gething, M.J. et al., "Variants of human tissue-type plasminogen activator . . . " The EMBO Journal, vol. 7, No. 9, S. 2731-2740 (1988).

Gill R et al."Pharmocological characterization of RO63-1908 (1-[2-(4-hydroxy-phenoxy)-ethyl]-4-(4-methyl-benzyl)-piperidin-4-01), a novel sinotype-selective N-methyl-D-asparatate antagonist" J Pharmacol. Exp. Ther. 302: 940-948 (2002).

Goeddel DV et al. National Center for Biotechnology Information Accession No. AAA01378 (ncbi.nlm.nih.gov/entrez/viewer.fcgi?db=protein&val=269380, (1993).

Gotti B et al. "Ifenprodil and SL 82.0715 as cerebral anti-ischemic agents. Evidence for efficacy in models of focal cerebral ischemia" J. Pharmacol. Exp. Ther. 247: 1211-1221 (1988)—Abstract.

Granelli-Piperno, A and Reich, E. A study of proteases and protease inhibitor complexes in biological fluids. J. Exp. Med. 148: 223-234 (1974).

Hacke W et al. "Association of outcome with early stroke treatment: Pooled analysis of ATLANTIS, ECASS, and NINDS rt-Pa stroke trial" Lancet 363:768-774 (2004).

Hacke W et al. "Intravenous Thrombolysis with recombinant tissue plasminogen activator for acute hemispheric stroke" JAMA 274: 1017-1025 (1995).

Hacke W et al. "Randomised double-blind placebo-controlled trial of thrombolytic therapy with intravenous alterplase in acute ischaemic stroke (ECASS II)" Lancet 352: 1245-1251 (1998).

Hacke W et al. "The desmoteplase in acute ischemic stroke trial (DIAS),: A phase II MRI-based 9-hour window acute stroke thrombolysis trial with intravenous desmoteplase" Stroke 36: 66-73 (2005).

Higgins et al., "The effect of the one-chain to two-chain conversion in tissue plasminogen activator: characterization of mutations at position 275" Thromb. Res., 57(4):527-39 (1990)—Abstract.

Horrevoets et al. "The specific role of finger and kringle domains of tissue-type plasminogen activator during in vitro fibrinolysis" J. Biol. Chem. 269: 12639-12644 (1994).

Huang YY, Bach ME, Lipp HP, Zhuo M, Wolfer DP, Hawkins RD, Schoonjans L, Kandel ER, Godfraind JM, Mulligan R, Collen D, Carmeliet P. Mice lacking the gene encoding tissue-type plasminogen activator show a selective interference with late-phase long-term, potentiation P.N.A.S. USA, 93: 8699-8704. (1996).

International Search Report for PCT/EP2004/004776 dated Aug. 24, 2004.
International Search Report for PCT/EP2004/010220 dated Jul. 12, 2005.
International Search Report for PCT/EP2002/12204 dated May 19, 2003.
International Search Report for PCT/EP2004/004626 dated Dec. 30, 2004.
Karonen JO, et al., "Combined diffusion and perfusion mri with correlation to single-photon emission ct in acute ischemic stroke" Ischemic penumbra predicts infarct growth. Stroke.; 30:1583-1590 (1999).
Ke SH et al. "Identification of a hydeophabic exosite . . . "J. Biol. Chem. 17.01.1997, vol. 272 Nr. 3, pp. 1816.
Kemp JA and McKernan RM NMDA Receptor Pathways as Drug Targets, Nat. Neurosci. 5: s1039-1042 (2002).
Keyt et al., "A faster-acting and more potent form of tissue plasminogen activator," PNAS USA 91: 3670-3674 (1994).
Krätzschmar J, Haendler B, Langer G, Boidol W, Bringmann P, Alagon A, Donner P, Schleuning WD. The plasminogen activator family from the salivary gland of the vampire bat Desmodus rotundus: cloning and expression. Gene 105:229-237 (1991).
Larsen GR et al. "Protein engineering of novel plasminogen activators with increased thrombolytic potency in rabbits relative to Activase" J. Biol. Chem. 266: 8156-8161 (1991).
Lee JM et al. "The changing landscape of ischaemic brain injury mechanisms" Nature 399(6738 Suppl): A7-14 (1999).
Lees, KR et al Glycine antagonist (gavestinel) in neuroprotection (GAIN Internatinal) in patients with acute stroke: a randomised controlled trial. GAIN International Investigators. Lancet 355: 1949-1954 (2000)—Abstract.
Lewandowski C, Wiliam Barsan, Treatment of Acute Stroke; in Annals of Emergency Medcine 37:2; S. 202 ff (2001).
Liberatore GT, et al., "Vampire bat salivary plasminogen activator (desmoteplase): A unique fibrinolytic enzyme that does not promote neurodegeneration" Stroke; 34:537-743 (2003).
Liu D "Tissue plasminogen activator neurovascular toxicity is controlled by activated protein C" Nat. Med. 10:1379-1383 (2004).
Madani R, Hulo S, Toni N, Madani H, Steimer T, Muller D, Vassalli JD. Enhanced hippocampal long-term potentiation and learning by increased neuronal expression of tissue-type plasminogen activator in transgenic mice. EMBO J.18:3007-3012 (1999).
Madison E et al. "Serpin-resistant mutants of human tissue-type plasminogen activator" Nature 339: 721-724 (1989).
Madison E L et al. "Converting tissue plasminogen . . . " Science, Bd. 262, 15.10. S. 419-421, XP000615414, S. 419, r Sp. Abs. 2 (1993).
Madison E. et al. "Amino acid residues that affect interaction of tissue-type plasminogen activator inhibitor 1", Proc. Natl. Acad. Sci. 87: 3530-3533 (1990).
Madison E.L. et al."Restoration of Serine Protease-Inhibitor Interaction by Protein engineering" J. Biol. Chem. 265: 21423-21426 (1990).
Martin U., et al.: "A novel recombinant plasminogen activator" Cardiovascular drug reviews; 11:299-311 (1993).
Matrai et al., "Activation pathway analysis of Rat-{Delta}-{alpha}-chymotrypsin by MD and TMD methods" FEBS Journal 272:s1 (2005)—Abstract.
Meden P; Tatlisumak T; Takano K; Carano RAD; Hadley SJ; Fisher M: Thrombolysis with recombinant Desmodus saliva plasminogen activator (rDSPA) in a rat embolic stroke model; in: Cerebrovasc Dis ; 175-194 (4th International Symposium on Thrombolic Therapy—Abstract.
Molina CA et al., "Thrombolyis-related hemorrhagic infarction: A maker of early reperfusion, reduced infarct size, and improved outcome in patients with proximal middle cerebral artery occlusion" Stroke 33:1551-1556 (2002).
Müller, C.M., Griesinger, C.B. "Tissue plasminogen activator mediates reverse occlusion plasticity in visual cortex" Nat. Neurosci. 1:47-53 (1998).
Muschick, P., et al., "Thrombolytic properties of Desmodus (vampire bat) salivary plasminogen activator DSPAα1, alteplase and streptokinase following intravenous bolus injection in a rabbit model of carotid artery thrombolysis," Fibrinolysis, 7:284-290 (1993).

Nicole, O., Docagne, F., Ali, C., Margaill, I., Carmeliet, P., MacKenzie, E.T., Vivien, D. & Buisson, A. The proteolytic activity of tissue-plasminogen activator enhances NMDA receptor-mediated signaling. Nat Med 7, 59-64 (2001).
Office Action, U.S. Appl. No. 10/494,004, Oct. 31, 2005.
Office Action, U.S. Appl. No. 10/494,004, Nov. 16, 2006.
Office Action, U.S. Appl. No. 10/494,004, Mar. 30, 2007.
Office Action, U.S. Appl. No. 10/494,004, Jul. 18, 2006.
Office Action, U.S. Appl. No. 11/264,088, Jan. 26, 2007.
Paoni NF et al. "Making tissue-type plasminogen activator more fibrin specific" Protein Engineering 6: 529-534 (1993).
Paoni, NF et al:: Thromb. Haemostas. 70:307-312 (1993).
Pawlak R, Magarinos AM, Melchor J, McEwen B, Strickland S "Tissue plasminogen activator in the amygdala is critical for stress-induced anxiety-like behavior" Nat. Neurosci. 6: 168-174 (2003)—Abstract.
Pawlak R, Nagal N, Urano T, Napiorkowska-Pawlak D, Ihara H, Takada Y, Collen D, Takada A "Rapid, specific and active site-catalyzed effect of tissue-Plasminogen activator on hippocampus-dependent learning in mice" Neuroscience 113: 995-1001 (2002)—Abstract.
Peck P "Bat drug extends stroke treatment time" United Press International (posted Feb. 3, 2004).
Petrovan et al., "Role of residue Phe225 in the cofactor-mediated, allosteric regulation of the serine protease coagulation factor VIIa" Biochemistry, 39(47):14457-63 (2000)—Abstract.
Reddrop C. et al. "Vampire bat salivary plasminogen activator (desmoteplase) inhibits tissue-type plasminogen activator-induced potentiation of excitotoxic injury" Stroke 36:1241-1246 (2005).
Renatus et al., "Catalytic domain structure of vampire bat plasminogen activator: a molecule paradigm for proteolysis without activation cleavage," Biochem 36:13483-13493 (1997)—Abstract.
Rijken DC et al. "Receptor-mediated endocytosis of tissue type plasminogen activator (t-PA) by liver cells" Thromb. Res.; Supel. X:63-71 (1990)—Abstract.
Ringleb PA et al. "Thrombolytic Therapy within 3 to 6 hours after onset of Ischemic stroke" Stroke 33: 1437-1441 (2002).
Rogove AD, Siao C, Keyt B, Strickland S, Tsirka SE. Activation of microglia reveals a non-proteolytic cytokine function for tissue plasminogen activator in the central nervous system. J Cell Sci 112:4007-4016 (1999).
Sacco RL et al. "Glycine antagonist in neuroprotection for patients with acute stroke: GAIN Americas: a randomized controlled trial." JAMA 285: 1719-1728 (2001)—Abstract.
Schleuning WD, Alagon A, Boidol W, Bringmann P, Petri T, Kratzschmar J, Haendler B, Langer G, Baldus B, Witt W, et al. Plasminogen activators from the saliva of Desmodus rotundus (common vampire bat): unique fibrin specificity. Ann N. Y Acad Sci 667:395-4 (1992).
Schleuning W-D: Vampire bat plasminogen activator DSPA-Alpha-1 (Desmoteplase): A thrombolytic drug optimized by natural selection Haemostasis 31: 118-122 (2001).
Seeds, N. W., Williams, B.L., Bickford, P.C. Tissue plasminogen activator induction in purkinje neurons after cerebellar motor learning. Science. 270:1992-1994 (1995).
Smalling RW "Molecular biology of plasminogen activators: what are the clinical implications of drug design?" Thromb. Haemostas. 70:307-312 (1993)—Abstract.
Sottrup-Jensen et al., "Amino-acid sequence of activation cleavage site in plasminogen: homology with 'pro' part of prothrombin" Proc. Natl. Acad. Sci. 72(7):2577-81 (1975)—Abstract.
Stewart Rj, Fredenburgh JC, Weitz JI. Characterization of the interactions of plasminogen and tissue and vampire bat plasminogen activators with fibrinogen, fibrin, and the complex of D-dimer noncovalently linked to fragment E. J Biol Chem 273:18292-18299, (1998).
Strandberg L. et al.: "Variants of tissue-type plasminogen . . . " Journ. of Biol. Chem., (1995) vol. 270, No. 40, pp. 23444-23449.
Tachias K et al. "Variants of tissue-type plasminogen" J. Biol. Chem. 270: 18319-18322 (1995).
Tate et al., "Functional role of proteolytic cleavage at arginine-275 of human tissue plasminogen activator as assessed by site-directed mutagenesis" Biochemistry, 26(2):338-43 (1987)—Abstract.

Thomson A: "New Thrombolytic drugs" AU and NZ Journ. of Medicine, vol. 29, Nr. 3, (1999), pp. 433-435.
Tiefenbrunn AJ, et al. "Clinical Pharmacology in patients with evolving myocartinal " Circulation, 71:110-116 (1985).
Toschi L, Bringmann P, Petri T, Donner P, Schleuning WD. Fibrin selectivity of the isolated protease domains of tissue-type and vampire bat salivary gland plasminogen activators. Eur J Biochem 252:108-112 (1998).
Traynelis, SF, Lipton, SA. Is tissue plasminogen activator a threat to neurons? Nature Medicine, 7:17-18 (2001).
Tsirka SE, Bugge TH, Degen JL, Strickland S. Neuronal death in the central nervous system demonstrates a non-fibrin substrate for plasmin. Proc Natl Acad Sci USA 94:9779-9781 (1997).
Tsirka SE, Gualandris A, Amaral DG, Strickland S. Excitotoxin-induced neuronal degeneration and seizure are mediated by tissue plasminogen activator. Nature. 377:340-344 (1995).
Tsirka SE, Rogove AD, Bugge TH, Degen JL, Strickland S. An extracellular proteolytic cascade promotes neuronal degeneration in the mouse hippocampus. J Neurosci 17:543-552 (1997).
Tsirka, S., Rogove, A. D., and Strickland, S. Neuronal cell death and tPA. Nature 384: 123-124 (1996).
van Gijn J, MD, FRCP,—Circulation 1996, 93: 1616-1617 (1996).
Verheyden et al., "A fluorescence stopped-flow kinetic study of the conformational activation of ?-chymotrypsin and several mutants" Protein Science 13:2533-2540 (2004).
Walker JB, Nesheim ME. A kinetic analysis of the tissue plasminogen activator and DSPAalphaI cofactor activities of untreated and TAFIa-treated soluble fibrin degradation products of varying size. J Biol Chem 276:3138-3148 (2001).
Wang YF, Tsirka SE, Strickland S, Stieg PE, Soriano SG, Lipton SA. Tissue plasminogen activator (tPA) increases neuronal damage after focal cerebral ischemia in wild-type and tPA-deficient mice. Nat Med. 4:228-231 (1998).
Warach S., "Thrombolysis in stroke beyond three hours: Targeting patients with diffusion and perfusion" MRI. Ann. Neurol.;51:11-13 (2001).
Weening-Verhoeff et al.: "Involvement of Aspartic and glutamic residues . . . " Protein engineering, Bdn. 269, Nr. 17;2 pp. 12639-12644 (1994).
Witt W, Maass B, Baldus B, Hildebrand M, Donner P, Schleuning WD. Coronary thrombolysis with *Desmodus* salivary plasminogen activator in dogs. Fast and persistent recanalization by intravenous bolus administration. Circulation. 90:421-426 (1994).
Witt, W, et al., "Thrombolytic Properties of *Desmodus rotundus* (vampire bat) Salivary Plasminogen Activator in Experimental Pulmonary Embolism in Rats" Blood 79:1213-1217 (1992).
Zhang et al., "Postischemic intracarotid treatment with TNK-tPA reduces infarct volume and improves neurological deficits in embolic stroke in the unanesthetized rat," Brain Res 878:64-71 (2000).
Press Release, "Paion sees continued development rationale for desmoteplase based on findings from phase III analysis," 3 pages (Oct. 18, 2007).
Desmoteplase (DSPA), Paion's non-confidential information, 9 pages (Nov. 2007).
Press Release, "Paion is seeking a new US-partner for desmoteplase," 2 pages (Nov. 12, 2007).
Baldus, B., "Thrombolysis of cerebral clots with desmodus salivary plasminogen activator alpha1 (DSPAalpha1) compared to alteplase in a rabbit model of embolic stroke," Thromb. Haemostasis, 73(6):1398 (1995).
Paoni, Nicholas F., et al., A slow clearing, fibrin-specific. PAI-1 resistant variant of t-PA (T103N. KHRR 296-299 AAAA), Thrombosis and Haemostasis, 70(2):307-312 (1993).
Office Action from U.S. Appl. No. 10/494,004, dated Jul. 24, 2007.
Office Action from U.S. Appl. No. 10/494,004, dated Jun. 1, 2007.
Office Action from U.S. Appl. No. 10/494,004, dated May 22, 2006.
Gardell, S., et al., Effective Thrombolysis without marked plasminemia after bolus intravenous administration of vampire bat salivar plasminogen activator in rabbits, Circulation 84:244-253 (1991).
Gardell, S., et al., "Isolation, characterization, and cDNA cloning of a vampire bat salivary plasminogen activator," The Journal of Biological Chemistry, 264(20):17947-17952 (1989).

Exhibit DD—Adams et al., "Guidelines for the early management of adult with ischemic stroke: A guideline from the American Heart Association/American Stroke Association Stroke Council, Clinical Cardiology Council, Cardiovascular Radiology and Intervention Council, and the Atherosclerotic Peripheral Vascular Disease and Quality of care Outcomes in Research Interdisciplinary Working Groups: The American Academy of Neurology affirms the value of this guideline as an educational tool for neurologists," Stroke, vol. 38, pp. 1655-1711 (2007) Reference submitted on Feb. 3, 2011 in co-pending U.S. Appl. No. 12/196,785.
Exhibit EE—Hacke et al., "Thrombolysis with Alteplase 3 to 4.5 hours after acute ischemic stroke," The New England Journal of Medicine, vol. 359, pp. 1317-1329 (Sep. 25, 2008) Reference submitted on Feb. 3, 2011 in co-pending U.S. Appl. No. 12/196,785.
Exhibit FF—Steiner et al., "The ECASS 3-hour Cohort, Secondary Analysis of ECASS Data by Time Stratification," Cerebrovascular Diseases, vol. 8, pp. 198-203 (1998) Reference submitted on Feb. 3, 2011 in co-pending U.S. Appl. No. 12/196,785.
Exhibit GG—The European Stroke Organization (ESO) Executive Committee and the ESO Writing Committee, "Guidelines for management of Ischaemic stroke and Transient Ischaemic Attack 2008," Cerebrovascular Diseases, vol. 25, pp. 457-507 (2008) Reference submitted on Feb. 3, 2011 in co-pending U.S. Appl. No. 12/196,785.
Exhibit HH—Del Zoppo et al., "Expansion of the time window for treatment of acute ischemic stroke with intravenous tissue plasminogen activator. A science advisory from the American Heart Association/American Stroke Association," Stroke, vol. 40, pp. 2945-2948 (2009) Reference submitted on Feb. 3, 2011 in co-pending U.S. Appl. No. 12/196,785.
Exhibit JJ—Ingall et al, "Findings From the Reanalysis of the NINDS Tissue Plasminogen Activator for Acute Ischemic Stroke Treatment Trial," Stroke, vol. 35, pp. 2418-242 (2004) Reference submitted on Feb. 3, 2011 in co-pending U.S. Appl. No. 12/196,785.
Exhibit KK—Muir, "The Impact of the Extended Time Window Seen in the ECASS III Trial on the Guidelines for Stroke Management in Europe," ENJ, vol. 1, pp. 1-5 (2009) Reference submitted on Feb. 3, 2011 in co-pending U.S. Appl. No. 12/196,785.
Notice of allowance mailed Feb. 18, 2011 for U.S. Appl. No. 12/196,785, filed Aug. 22, 2008.
Desmoteplase (DSPA) publication from PAION from 2007.
Jones et al., "Trends in the Treatment of Coronary Disease Today. Selective use of PTCA and Bypass Surgery" Ann. Surg., vol. 197(6), pp. 728-736 (Jun. 1983).
Maulaz et al. "Selecting patients for early stroke treatment with penumbra images," Cerebrovasc Dis., vol. 20, suppl 2, pp. 19-24 (2005).
Weening-Verhoeff et al., "Involvement of aspartic and glutamic residues in kringle-2 of tissue-type plasminogen activator in lysine binding, fibrin binding and stimulation of activity as revealed by chemical modification and oligonucleotide-directed mutagenesis," Protein Engineering, vol. 4(2); pp. 191-198 (1990).
English Abstract for WO 03/037363, dated May 8, 2003.
International Search Report and Written Opinion mailed on Jun. 8, 2009 for International Application No. PCT/EP2008/008871.
Mebs, "Gifttiere Ein Handbuch fur Biologen, Toxikologen, Arzte und Apotheker," Wissenschaftliche Verlagsgesellschaft mbH, Stuttgart , p. 1-33 (2000)—English translation for pp. 19-21.
Forth, Henschler, Rummel and Starke, "Pharmakologie und Toxikologie," 6 Auflage, Wissenschaftsverlag Mannheim, Leipzig, Wien, Zurich, S. 29 (1992)—English Translation.
Mutschler, "Arzneimittelwirkungen," 8 Auflage, Wissenschaftliche Verlagsgesellschaft, Stuttgart, S. 512-513 (2001)—English translation.
U.S. Appl. No. 13/011,214, Sohngen et al.
Chesebro et al., "Thrombolysis in Myocardial Infarction (TIMI) Trial, Phase I: A comparison between intravenous tissue plasminogen activator and intravenous streptokinase. Clinical findings through hospital discharge," Circulation , vol. 76, pp. 142-154 (1987).
"Vampire Bat spit could help stroke victims," Discovery Health Channel at health.discovery.com/news, posted Jan. 10, 2003.
Interview Summary dated Feb. 11, 2011 for U.S. Appl. No. 12/196,785.

Alexandrov et al., "Speed of intracranial clot lysis with intravenous tissue plasminogen activator therapy," Circulation, vol. 103, pp. 2897-2902 (2001).

Alexandrov et al., "High rate of complete recanalization and dramatic clinical recovery during tPA infusion when continuously monitored with 2-MHz transcranial doppler monitoring," Stroke, vol. 31, pp. 610-614 (2000).

Andersen et al., "Effects of citicoline combined with thrombolytic therapy in a rat embolic stroke model," Stroke, vol. 30, pp. 1464-1471 (1999).

Demchuk et al., "Thrombolysis in brain ischemia (TIBI) transcranial doppler flow grades predict clinical severity, early recovery, and mortality in patients treated with intravenous tissue plasminogen activator," Stroke, vol. 32, pp. 89-93 (2001).

Felberg et al., "Early dramatic recovery during intravenous tissue plasminogen activator infusion," Stroke, vol. 33, pp. 1301-1307 (2002).

Written Opinion mailed on Jun. 8, 2009 for International Application No. PCT/EP2008/008871.

* cited by examiner

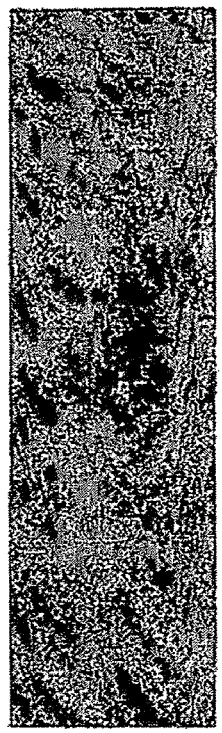
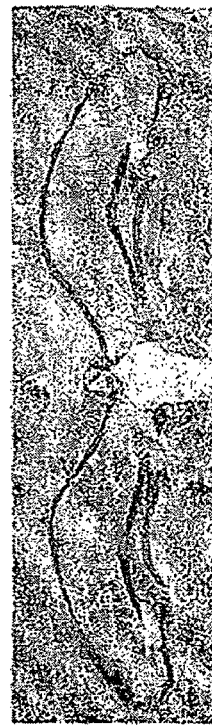
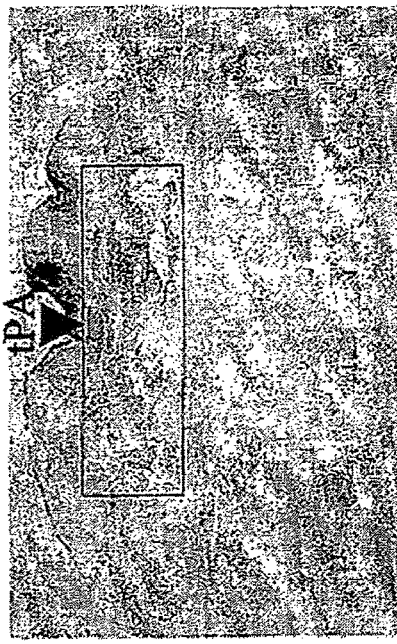
Fig. 2
tPA -/- mouse after tPA infusion

Neuronal survival in the hippocampus

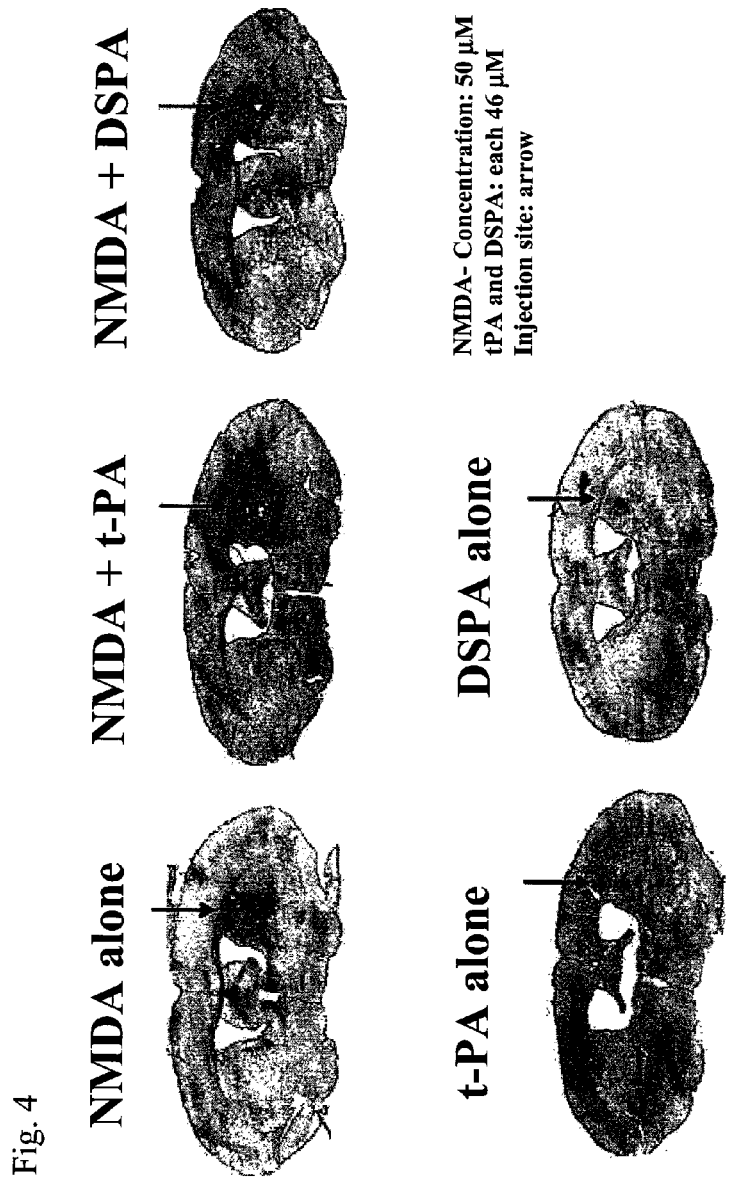
DSPA does not enhance NMDA-mediated neurodegeneration in the mouse striatum
Competitive advantage vs rt-PA

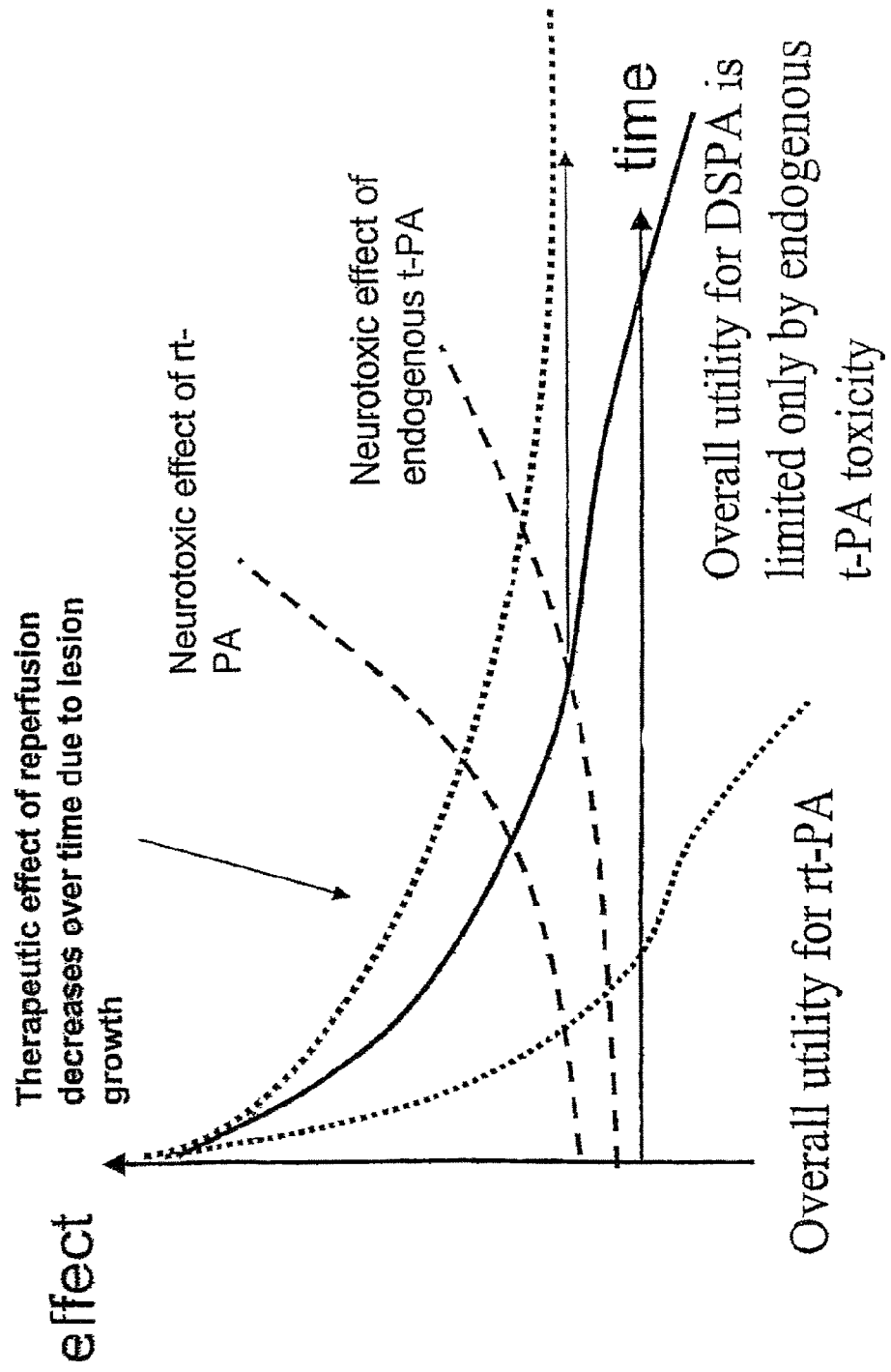
Fig. 5 Constant relative increase of t-PA Neurotoxicity is time limiting for therapy and "additive" to rt-PA Neurotoxicity

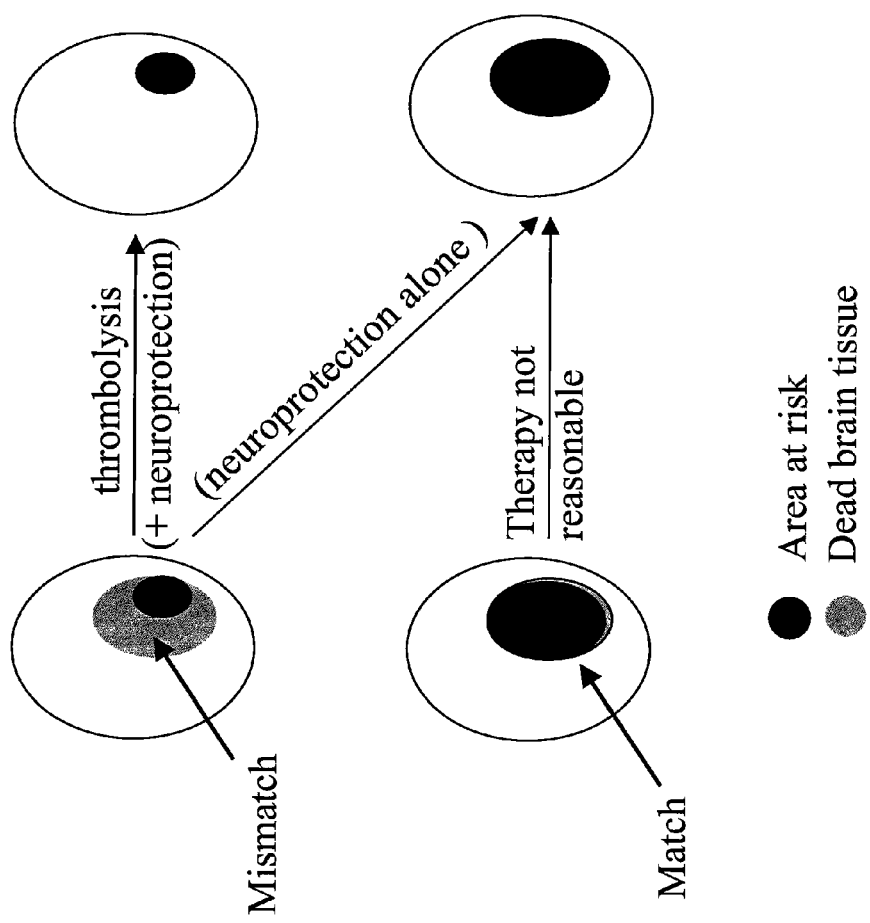

Fig. 9

SEQ. ID Nr. 2

```
  1  MVNTMKTKLL  CVLLLCGAVF  SLPRQETYRQ  LARGSRAYGV  ACKDEITQMT
 51  YRRQESWLRP  EVRSKRVEHC  QCDRGSNELH  QVPSNSCDEP  RCLNGGTCVS
101  NKYFSIHWCN  CPKKFGGQHC  EIDKSKTCYE  GNGHFYRGKA  STDTMGRPCL
151  PWNSATVLQQ  TYHAHRSDAL  QLGLGKHNYC  RNPDNRRRPW  CYVQVGLKPL
201  VQECMVHDCA  DFQCGQKTLR  EPRFHSTGGE  FTTIENQPWF  AAIYRRHRGG
251  SGVTYVCGGS  LMSPCWVISA  THCFIDYPKK  EDYIVYLGRS  RLNSNTQGEM
301  KFEVENLILH  KDYSADTHHN  DIALLKIRSK  EGRCAQPSRT  IQTICLPSMY
351  NDPQFGTSCE  ITGFGKENST  DYLYPEQLKM  TVVKLISHRE  CQQPHYYGSE
401  VTTKMLCAAD  PQWKEIYPNV  TDSCQGDSGG  PLVCSLQGRM  TLTGIVSWGR
451  GCALKDKPGV  YTRVSHFLPW  IRSHTKL
```

Fig. 10

SEQ. ID Nr. 1

```
  1  MVNTMKTKLL  CVLLLCGAVF  SLPRQETYRQ  LARGSRAYGV  ACKDEITQMT
 51  YRRQESWLRP  EVRSKRVEHC  QCDRGQARCH  TVPVKSCSEP  RCFNGGTCQQ
101  ALYFSDFVCQ  CPEGFAGKCC  EIDTRATCYE  DQGISYRGTW  STAESGAECT
151  NWNSSALAQK  PYSGRRPDAI  RLGLGNHNYC  RNPDRDSKPW  CYVFKAGKYS
201  SEFCSTPACS  STCGLRQYSQ  PQFHSTGGLF  ADIASHPWQA  AIFAKHRRSP
251  GERFLCGGIL  ISSCWILSAA  HCFQERFPPH  HLTVILGRTY  RVVPGEEEQK
301  FEVEKYIVHK  EFDDDTYDND  IALLQLKSDS  SRCAQESSVV  RTVCLPPADL
351  QLPDWTECEL  SGYGKHEALS  PFYSERLKEA  HVRLYPSSRC  TSQHLLNRTV
401  TDNMLCAGDT  RSGGPQANLH  DACQGDSGGP  LVCLNDGRMT  LVGIISWGLG
451  CGQKDVPGVY  TKVTNYLDWI  RDNMRP
```

NON-NEUROTOXIC PLASMINOGEN ACTIVATING FACTORS FOR TREATING STROKE

RELATED APPLICATION

This is a continuation of application Ser. No. 11/311,475, filed on Dec. 20, 2005, now abandoned, which is a continuation of application Ser. No. 10/184,018, filed Jun. 28, 2002, now abandoned, which claims the benefit of priority to German Patent Application No. 101 53 601.1, filed on Nov. 2, 2001, and European Patent Application No. 01 130 006.8 filed on Dec. 17, 2001. All applications mentioned in this paragraph are incorporated herein by reference.

FIELD OF THE INVENTION

The invention pertains to the therapeutic use of non-neurotoxic plasminogen activators especially from the saliva of *Desmodus rotundus* (DSPA) preferentially for the treatment of stroke.

BACKGROUND OF THE INVENTION

The term "stroke" is a general term that covers conditions having different clinical symptoms. For example, a stroke may be caused by an ischaemic or haemorrhagic insult.

Ischaemic insults (ischaemia) are characterized in a reduction or interruption of the blood circulation in the brain due to a lack of arterial blood supply. Often this is caused by thrombosis of an arteriosclerotic stenosed vessel or by arterio arterial, or cardial embolisms.

Haemorrhagic insults are based inter alia on the perforation of brain supplying arterias damaged by arterial hypertonia. However, only approximately 20% of all cerebral insults are caused by haemorrhagic insults. Thus, stroke due to thrombosis is much more prevalent.

In comparison to other tissue ischaemias, the ischaemia of the neuronal tissue is widely accompanied by necrosis of the effected cells. The higher incidence of necrosis in neuronal tissue can be explained with the new understanding of the phenomenon "excitotoxicity," which is a complex cascade comprising a plurality of reaction steps. The cascade is initiated by ischaemic neurons affected by a lack of oxygen, which then lose ATP instantaneously and depolarize. This results in an increased postsynaptic release of the neurotransmitter glutamate, which activates membrane bound glutamate receptors regulating cation channels. However, due to the increased glutamate release glutamate receptors become over activated.

Glutamate receptors regulate voltage dependent cation channels, which are opened by a binding of glutamate to the receptor. This results in a $Na^+$ and $Ca^{2+}$ influx into the cell massively disturbing the $Ca^{2+}$ dependent cellular metabolism. Especially the activation of the $Ca^{2+}$ dependent catabolic enzymes result in subsequent cell death (Lee, Jin-Mo et al., "The changing landscape of ischaemic brain injury mechanisms"; Dennis W. Zhol "Glutamate neurotoxicity and diseases of the nervous system").

Although the mechanism of glutamate mediated neurotoxicity is not yet entirely understood, it is agreed upon that it contributes in a large extent to neuronal cell death following cerebral ischaemia (Jin-Mo Lee, et al.).

The re-opening of a closed vessel has priority in the therapy of acute cerebral ischaemia, in addition to safeguarding vital functions and stabilizing physiological parameters. The re-opening can be performed by different means. The mere mechanical re-opening, as e.g., Percutaneous Transluminal Coronary Angioplasty (PTCA) after heart attack, so far has not yet led to satisfying results. Only with a successful fibrinolysis can an acceptable improvement of the physical condition of patients be achieved. This can be accomplished by a local application using a catheter (PROCAT, a study with pro-urokinase). However, despite initial positive results, this method has not yet been officially approved as a pharmaceutical treatment.

Naturally occurring fibrinolysis is based on the proteolytic activity of the serine protease plasmin, which originates from its inactive precursor by catalysis (activation). The natural activation of plasminogen is catalyzed by the plasminogen activators u-PA (urokinase type plasminogen activator) and t-PA (tissue plasminogen activator) occurring naturally in the body. In contrast to u-PA, t-PA forms a so-called activator complex together with fibrin and plasminogen. Thus, the catalytic activity of t-PA is fibrin dependent and is enhanced in its presence approximately 550-fold. Besides fibrin, fibrinogen can also stimulate t-PA mediated catalysis of plasminogen to plasmin, though to a lesser extent. In the presence of fibrinogen, the t-PA activity only increases 25-fold. Also the cleavage products of fibrin (fibrin degradation products (FDP)) can stimulate t-PA.

Early attempts of thrombolytic treatment of acute stroke go back to the 1950s. Extensive clinical trials with streptokinase, a fibrinolytic agent from beta-haemolysing streptococci, started in 1995. Streptokinase forms a complex with plasminogen that catalyzes other plasminogen molecules into plasmin.

Streptokinase therapy has severe disadvantages since streptokinase is a bacterial protease and therefore can provoke allergic reactions in the body. Furthermore, if a patient had a previous streptococci infection that resulted in a production of antibodies, the patient may exhibit streptokinase resistance, making the therapy more difficult. Besides this, clinical trials in Europe (Multicenter Acute Stroke Trial of Europe (MAST-E), Multicenter Acute Stroke Trial of Italy (MAST-I)) and Australia (Australian Streptokinase Trial (AST)) indicated an increased mortality risk and a higher risk of intracerebral bleeding (intracerebral haemorrhage, ICH) after treating patients with streptokinase. These trials had to be terminated early.

Alternatively, urokinase—also a classical fibrinolytic agent—can be used. In contrast to streptokinase, it does not exhibit antigenic characteristics since it is an enzyme naturally occurring in various body tissues. It is an activator of plasminogen and independent of a co-factor. Urokinase is produced in kidney cell cultures.

Another therapeutic thrombolysis agent tested was a recombinant tissue type plasminogen activator, rt-PA (see EP 0 093 619, U.S. Pat. No. 4,766,075), produced in recombinant hamster cells. In the 1990s several clinical trials were performed world-wide using t-PA with acute myocardial infarction as the main indication, leading to only partially understood and contradictory results. In the European Acute Stroke Trial (ECASS) patients were treated within a time frame of 6 hours after the onset of the symptoms of a stroke intravenously with rt-PA. After 90 days the mortality rate as well as the Barthel-Index were examined as an Index for the disability or the independent viability of patients. No significant improvement of the viability was reported but an increase of mortality was seen. Thus, a thrombolytic treatment with rt-PA of patients being individually selected according to their respective case history immediately after the beginning of the stroke could possibly be advantageous. However, a general use of rt-PA within the time frame of 6 hours after the onset of stroke was not recommended since an application during this time increased the risk of intracerebral haemorrhage (ICH) (C. Lewandowski C and Wiliam Barsan, 2001: Treatment of Acute Stroke; in: Annals of Emergency Medicine 37:2; S. 202 ff.).

The thrombolytic treatment of stroke was also subject of a clinical trial conducted by the National Institute of Neurologic Disorder and Stroke (so called NINDS rtPA Stroke Trial) in the USA. This trial concentrated on the effect of intravenous rt-PA treatment within only three hours after the onset of the symptoms. Patients were examined three months after the treatment. Due to the observed positive effects of this treatment on the viability of patients rt-PA treatment-within the limited time frame of three hours was recommended, although the authors found a higher risk for ICH.

Two further studies (ECASS II Trial: Alteplase Thrombolysis for Acute Noninterventional Therapy in Ischaemic Stroke (ATLANTIS)) examined whether the positive effects of rt-PA treatment within three hours after the onset of stroke could be repeated instead with a treatment within six hours time. However, the results indicated that there was no improvement in the clinical symptoms, nor was there any decrease in mortality. Further, the higher risk for ICH remained.

These partially contradictory results led to a high caution in the use of rt-PA. A 1996 publication of the *American Heart Association* pointed out the strong skepticism among doctors with respect to thrombolytic treatment of stroke; in contrast, there is no such skepticism with respect to fibrinolytica in the therapy of myocardical infarct (van Gijn J, MD, FRCP, 1996-Circulation 1996, 93: 1616-1617).

A rationale behind this skepticism was first given in a summary of all stroke trials published 1997 (updated in March 2001). According to this review all thrombolytica treatments (urokinase, streptokinase, rt-PA or recombinant urokinase) resulted in a significant higher mortality within the first 10 days after a stroke, while the total number of either dead or disabled patients was reduced when the thrombolytica were applied within six hours after stroke onset. This effect was mainly due to ICH. Such results gave reason to some to make the sarcastic statement that stroke patients had the choice to either die or to survive disabled (SCRIP 1997: 2265, 26). The broad use of thrombolytica for the treatment of stroke was therefore not recommended.

Nevertheless, the therapy with rt-PA currently is the only treatment of acute cerebral ischaemia approved by the Food and Drug Administration (FDA) in the USA. However, it is restricted to administration within three hours after the onset of stroke.

The approval of rt-PA was reached in 1996. In 1995, first announcements about negative side effects of t-PA became known, which provide an explanatory basis for its dramatic effects when applied in stroke treatment outside the three hour time frame. Microglia cells and neuronal cells of the hippocampus produce t-PA, which contributes to the glutamate mediated excitotoxicity. This was concluded from a comparative study on t-PA deficient and wild type mice where glutamate agonists were injected in their hippocampuses. The t-PA deficient mice showed a significant higher resistance against external (inthrathecal) applicated glutamate (Tsirka S E et al., Nature, Vol. 377, 1995, "Excitoxin-induced neuronal degeneration and seizure are mediated by tissue plasminogen activator"). These results were confirmed in 1998, when Wang et al. demonstrated a nearly double quantity of necrotic neuronal tissue in t-PA deficient mice when t-PA was injected intravenously. This negative effect of external t-PA on wild type mice was only approximately 33% (Wang et al., 1998, Nature, "Tissue plasminogen activator (t-PA) increases neuronal damage after focal cerebral ischaemia in wild type and t-PA deficient mice".)

Further results on the stimulation of excitotoxicity by t-PA were published by Nicole et al. in the beginning of 2001 (Nicole O., Docagne F Ali C; Margaill I; Carmeliet P; MacKenzie E T, Vivien D and Buisson A, 2001: The proteolytic activity of tissue-plasminogen activator enhances NMDA receptor-mediated signaling; in: Nat Med 7, 59-64). They showed that t-PA being released by depolarized cortical neurons could interact with the NR1 sub-unit of the glutamate receptor of the NMDA type, leading to a cleavage of NR1. This increased the receptor's activity, resulting in greater tissue damage after glutamate agonist NMDA was applied. The NMDA agonist induced excitotoxicity. Thus, t-PA exhibits a neurotoxic effect by activating the glutamate receptor of the NMDA type.

According to a further explanation, the neurotoxicity of t-PA results indirectly from the conversion of plasminogen in plasmin. According to this model plasmin is the effector of neurotoxicity (Chen Z L and Strickland S, 1997: Neuronal Death in the hippocampus is promoted by plasmin-catalysed degradation of laminin. Cell: 91, 917-925).

An outline summarizing the time depending neurotoxic effect of t-PA is given in FIG. 5. The increased toxicity of the recombinant t-PA compared to endogenic t-PA is also evident in FIG. 5. This increased toxicity is probably due to rt-PA being able to enter into tissue in higher concentrations.

Despite its neurotoxic side effect and its increasing effect on mortality, t-PA was approved by FDA. This can only be explained by the lack of harmless and effective alternatives. Therefore, there is still a need for safe therapies. However, if they were still based on thrombolytica, in case it is not possible to find alternatives to thrombolysis, the problem of neurotoxicity has to be considered (see for example Wang et al. a.a.O.; Lewandowski and Barson 2001 a.a.O.).

Further examination of known thrombolytica including DSPA (*Desmodus rotundus* Plasminogen Activator) as possible new drug candidates for stroke was terminated, even though principally all thrombolytica were potentially suitable. The potential suitability of DSPA for this medical indication was pointed out earlier (Medan P; Tatlisumak T; Takano K; Carano R A D; Hadley S J; Fisher M: Thrombolysis with recombinant Desmodus saliva plasminogen activator (rDSPA) in a rat embolic stroke model; in: Cerebrovasc Dis 1996:6; 175-194 (4$^{th}$ International Symposium on Thrombolic Therapy in Acute Ischaemic Stroke). DSPA is a plasminogen activator with a high homology (resemblance) to t-PA. Therefore—and in addition to the disillusionment resulting from the neurotoxic side effects of t-PA—there were no further expectations for DSPA being a suitable drug for stroke treatment.

Instead, recent strategies aiming to improve known thrombolytic treatments tried to apply the thrombolytic substance intraarterially, rather than intravenously via a catheter positioned close to the intravascular thrombus. The initial experiments were performed with recombinant produced urokinase. The hope was that the necessary dose for thrombolysis could be reduced and that the negative side effects could be reduced. However, this application requires a high technical expenditure and is not available everywhere. Furthermore, the patient has to be prepared in a time consuming action. Time, however, is often limited when treating for stroke. Thus, the additional preparation time adds an additional risk.

Presently, new concepts are directed to anticoagulants such as heparin, aspirin or ancrod, which is the active substance in the poison of the malayan pit viper. Two clinical trials examining the effects of heparin (International Stroke Trial (IST) and Trial of ORG 10172 in Acute Stroke Treatment (TOAST)) however, did not indicate a significant improvement of mortality or a prevention of stroke.

A further new treatment did not focus on thrombus, blood thinning or anti coagulation, but instead attempted to increase the vitality of cells damaged by the interruption of blood supply (WO 01/51613 A1 and WO 01/51614 A1). To achieve this, antibiotics from the group of quinons, aminoglycosides or chloramphenicol were applied. In an alternative strategy, a research group administered citicholin immediately after the onset of stroke. In the body, citicholin is cleaved to cytidine and choline. The cleavage products form part of the neuronal cell membrane and thus support the regeneration of damaged tissue (U.S. Pat. No. 5,827,832).

Recent research on safe treatment is based on the new finding that a part of the fatal consequences of stroke is caused only indirectly by interrupted blood supply but directly to excito- or neurotoxicity, including over-activated glutamate receptors. This effect is increased by t-PA (see above). A strategy to reduce excitotoxicity would be, therefore, to administer neuroprotectives. Neuroprotectives can be used separately or in combination with fibrinolytic agents in order to minimize neurotoxic effects. They can lead to a reduced excitotoxicity either directly, e.g. as a glutamate receptor antagonist, or indirectly, e.g., by inhibiting voltage dependent sodium or calcium channels (Jin-Mo Lee et al. a.a.O.).

A competitive inhibition (antagonistic action) of the glutamate receptor of NMDA type can be achieved, e.g., with 2-amino-5-phosphonovalerate (APV) or 2-amino-5-phosphonoheptanoate (APH). A non competitive inhibition can be achieved, e.g., by substances binding to the phencyclidine side of the channels. Such substances can be phencyclidine, MK-801, dextrorphane or cetamine.

So far, treatments with neuroprotectives have not shown the expected success, possibly because neuroprotectives had to be combined with thrombolytic agents in order to exhibit their protective effects. This also applies to other substances (see also FIG. 6).

Even a combination of t-PA and neuroprotective agents results only in limited damage. Nevertheless, the disadvantageous neurotoxicity of the fibrinolytic agent as such is not avoided.

SUMMARY OF THE INVENTION

The present invention provides a new therapeutic treatment of stroke in humans.

According to the invention, a non-toxic plasminogen activating factor is administered for the therapeutic treatment of stroke.

The central idea of the invention is the use of a plasminogen activator in the treatment of stroke, of which the mature enzyme exhibits an activity, which can be selectively increased by fibrin manifold, such as by more than 650-fold.

The use of the plasminogen activators according to the invention is based on the finding that due to tissue damage in the brain caused by stroke, the blood brain barrier is damaged or destroyed. This damage to the blood brain barrier allows fibrinogen circulating in the blood to enter into the neuronal tissue of the brain. Once in the brain, it activates t-PA that indirectly activates the glutamate receptor or plasminogen, resulting in further tissue damage. In order to avoid this effect, the invention uses a plasminogen activator that is highly fibrin selective and has a reduced potential to be activated by fibrinogen. Thus, this plasminogen activator is not (or compared to t-PA at least is substantially less) activated by fibrinogen entering from the blood into neuronal tissue as a result of damaged blood brain barrier, since t-PAs activator fibrin cannot normally enter the neuronal tissue due to its size. The plasminogen activators according to the invention therefore are non-neurotoxic.

According to a preferred embodiment of the invention, non-toxic plasminogen activators are used, which comprise at least one element of the so called cymogene triade. A comparable triade is present in the catalytic center of serine proteases of the chymotrypsine family consisting of three interacting amino acids aspartate 194, histidine 40 and serine 32. However, this triade does not exist in t-PA which also belongs to the chymotrypsine family. Nevertheless, it is known, that the directed mutagenesis of native t-PA for the purpose of introducing at least one of the above amino acids at a suitable position results in a reduced activity of the pro-enzyme (single chain t-PA) and in an increased activity of the mature enzyme (double chain t-PA) in the presence of fibrin. Therefore, the introduction of at least one amino acid of the triade—or of an amino acid with the same function in the triade—can increase the cymogenity of t-PA (i.e. the ratio between the activity of the mature enzyme an the activity of the pro-enzyme). As a result the fibrin specificity of t-PA is remarkably increased. This is a result of the conformational interaction between the introduced amino acid residue and/or amino acid residues of the wild type sequence.

It is known that the mutagenesis of the native t-PA with substitution of Phe305 by His (F305H) and of Ala 292 by Ser (A292S) leads to a 20-fold increase of cymogenity, whereas the variant F305H alone already leads to 5-fold increase of r cymogenity (E L Madison, Kobe A, Gething M-J; Sambrook J F, Goldsmith E J 1993: Converting Tissue Plasminogen Activator to a Zymogen: A regulatory Triad of Asp-His-Ser, Science: 262, 419-421). In the presence of fibrin these t-PA mutants show an activity increase of 30,000 (F305H) and 130,000 (F305H, A292S) respectively. In addition these mutants comprise a substitution of Arg275 to R275E in order to prevent cleavage by plasmin at the cleavage site Aug275-Ile276, thereby converting the single chain t-PA into the double chain molecule. The mutant site R275E alone leads to a 6.900 fold increase of the fibrin specificity of t-PA (K Tachias, Madison E L 1995: Variants of Tissue-type Plasminogen Activator Which Display Substantially Enhanced Stimulation by Fibrin, in: Journal of Biological Chemistry 270, 31: 18319-18322).

The positions 305 and 292 of t-PA are homologous to the positions His40 and Ser32 of the known triade of chymotryptic serine proteases. A substitution introducing histidine and serine at the positions 305 and 292, these amino acids can interact with the aspartate 477 of t-PA resulting in a functional triade in the t-PA mutants (Madison et al., 1993).

These t-PA mutants can be used for the treatment of stroke according to the invention since they show no or—compared to wild type t-PA—a significantly reduced neurotoxicity due to their increased fibrin specificity. For the purpose of disclosure of the mentioned t-PA mutants F305H; F305H; A292S alone or in combination with R275E publications of Madison et al., (1993) and Tachias and Madison (1995) hereby are fully incorporated by reference.

The increase of fibrin specificity of plasminogen activators can alternatively be achieved by a point mutation of Asp194 (or an aspartate at a homologous position). Plasminogen activators belong to the group of serine proteases of the chymotrypsin family and therefore comprise the conserved amino acid Asp194, which is responsible for the stability of the catalytically active conformation of the mature proteases. It is known that Asp194 interacts with His40 in the cymogenic form of serine proteases. After the cymogene is activated by cleavage this specific interaction is interrupted and the side chain of the Asp194 rotates about 170° in order to form a new salt bridge with Ile16. This salt bridge essentially contributes to the stability of the oxyanione pocket of the catalytic center of the mature serine proteases. It is also present in t-PA.

The introduction of a point mutation replacing Asp194 prima facie impedes the formation or stability of the catalytic conformation of serine proteases. However, the mutated plasminogen activators show a significant increase of activity in the presence of their co-factor fibrin—especially in comparison to the mature wild type form. This can only be explained on the basis of the interaction with fibrin allowing a conformational change promoting catalytic activity (L Strandberg, Madison E L, 1995: Variants of Tissue-type Plasminogen Activator with Substantially Enhanced Response and Selectivity towards Fibrin co-factors, in: Journal of Biological Chemistry 270, 40: 2344-2349).

In conclusion, the Asp194 mutants of the plasminogen activators show a high increase of activity in presence of fibrin which allows their use according to the invention.

In a preferred embodiment according to the invention, a mutant t-PA is used, in which Asp194 is substituted by glutamate (D194E) or by asparagine (D194N). In these mutants the activity of t-PA is reduced 1 to 2000 fold in the absence of fibrin, whereas in the presence of fibrin, an increase of activity by a factor of 498,000 to 1,050,000 can be achieved. These mutants can further comprise a substitution of Arg15 to R15E, which prevents the cleavage of the single chain t-PA at the peptide bond Arg15-Ile16 by plasmin, leading to the double chain form of t-PA. This mutation alone increases the activation of t-PA by fibrin by the factor 12,000. For reasons of disclosure of the t-PA mutations at positions 194 and 15, the publications of Strandberg and Madison (1995) are fully incorporated by reference.

An increase of the fibrin dependency of plasminogen activators can also be achieved by the introduction of point mutations in the so called "autolysis loop". This element is known from trypsine; it can also be found as a homologous region in serine proteases and is especially characterized by three hydrophobic amino acids (Leu, Pro and Phe). The autolysis loop in plasminogen activators is responsible for the interaction with plasminogen. Point mutations in this area can have the effect that the protein-protein interaction between plasminogen and plasminogen activators cannot be effectively formed any longer. These mutations are only functionally relevant in the absence of fibrin. In the presence of fibrin, they, in contrast, are responsible for an increased activity of the plasminogen activators (K Song-Hua, Tachias K, Lamba D, Bode W, Madison E L, 1997: Identification of a Hydrophobic exocite on Tissue Type Plasminogen Activator That Modulates Specificity for Plasminogen, in: Journal of Biological Chemistry 272; 3, 1811-1816).

BRIEF DESCRIPTION OF THE FIGURES

FIG. 2 shows results indicating that t-PA and DSPA activity is recovered in hippocampal extracts prepared from t-PA −/− mice following infusion. See Results section B.2.

FIG. 4 shows results indicating that DSPA does not enhance NMDA-mediated neurodegeneration in the mouse striatum.

FIG. 5 shows the time-depending neurotoxic effect of t-PA and the increased toxicity of the recombinant t-PA compared to endogenic t-PA.

FIG. 6 shows salvageable tissue as a requirement for a successful treatment.

FIG. 9 shows the amino acid sequence of a modified uroquinase polypeptide (SEQ ID NO: 2).

FIG. 10 shows the amino acid sequence of a modified tissue plasminogen activator (SEQ ID NO: 1).

DETAILED DESCRIPTION

Figure 1:
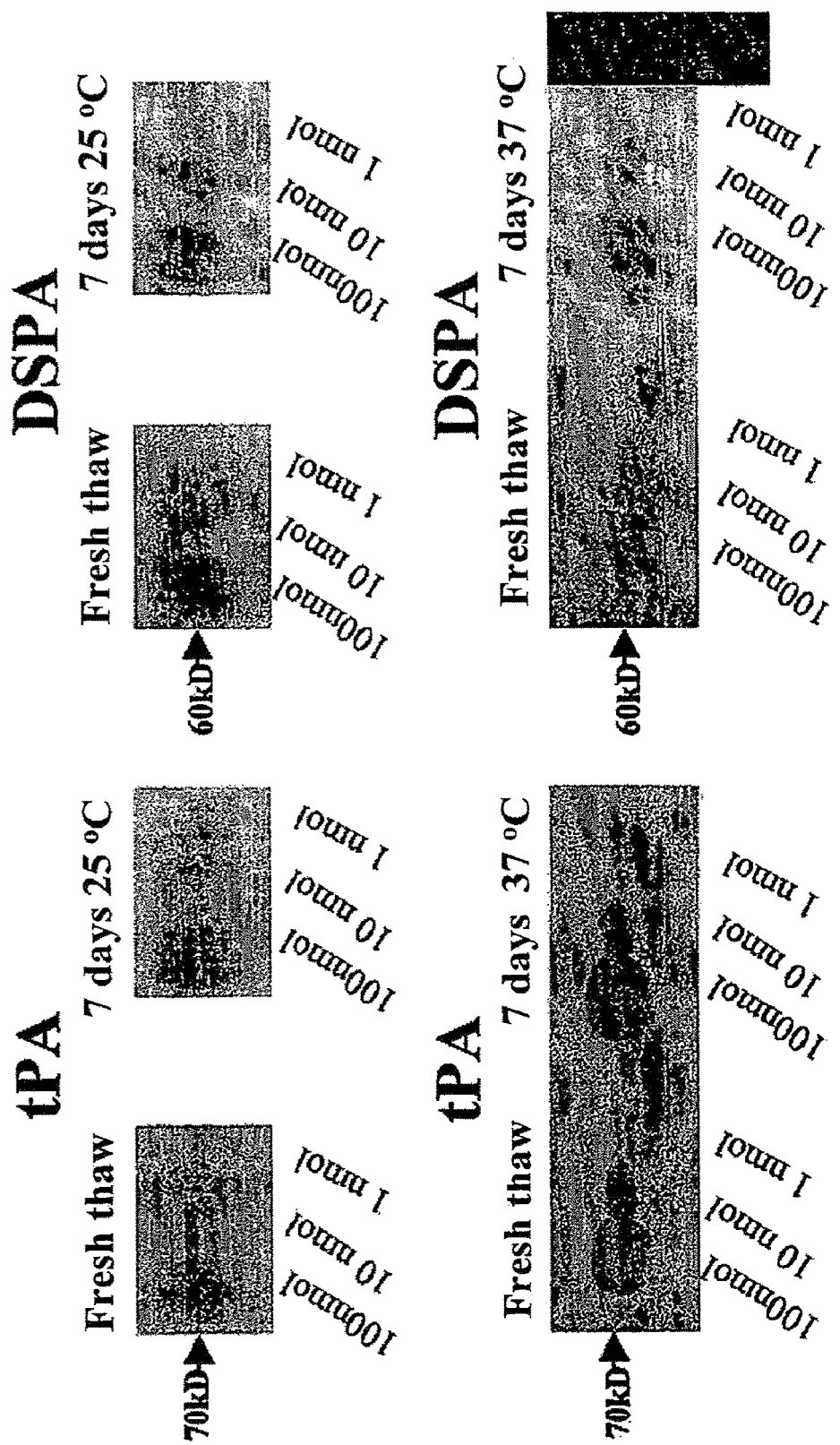
FIG. 1 shows results indicating that infusion of t-PA or DSPA disperses into the hippocampus of t-PA −/− mice and retains proteolytic activity. See Results section B.1.

In a preferred embodiment t-PA is used showing point mutations in the positions 420 to 423. If these residues are substituted by directed mutagenesis the fibrin dependency of t-PA is increased by a factor up to 61,000 (K Song-Hua et al.). Song-Hua et al. examined the point mutations L420A, L420E, S421G, S421E, P422A, P422G, P422E, F423A and F423E. These publications are fully incorporated by reference for disclosure of the use according to the invention.

According to a further advantageous embodiment a modified tissue plasminogen activator with an amino acid sequence according to SEQ ID No. 1 (FIG. 10) is used. This modified t-PA differs from the wild type t-PA by the exchange of the hydrophobic amino acids in the position 420 to 423 in the autolysis loop as follows: His420, Asp421, Ala422 and Cys423. This t-PA preferentially contains a phenyl alanine at the position 194. Further the position 275 can be occupied by glutamate. Advantageously the position 194 is occupied by phenyl alanine.

Furthermore, a modified urokinase can be used according to the invention. The urokinase according to the invention can comprise the amino acid sequence according to SEQ ID No. 2 (FIG. 9) in which the hydrophobic amino acids of the autolysis loop are substituted by Val420, Thr421, Asp422 and Ser423. Advantageously the urokinase is carrying an Ile275 and a Glu194. This mutant—in comparison to wild type urokinase—shows a 500-fold increased fibrin specificity.

Both mutants—urokinase as well as t-PA—were analyzed in semi quantitative tests and showed a increased fibrin specificity in comparison to the wild type t-PA.

The plasminogen activator (DSPA) from the saliva of the vampire bat (*Desmodus rotundus*) also shows a highly increased activity in the presence of fibrin—specifically a 100,000-fold increase. Thus it can be used as preferred embodiment of the invention. The term DSPA comprises four different proteases, which function to increase the duration of wound bleeding of pray (Cartwright, 1974). These four proteases (DSPAα1, DSPAα2, DSPAβ, DSPAγ) display a high similarity (homology) to each other and to the human t-PA. They also show similar physiological activities, leading to a common classification under the generic term DSPA. DSPA is disclosed in the patents EP 0 352 119 A1 and of U.S. Pat. Nos. 6,008,019 and 5,830,839 which are hereby fully incorporated by reference for purpose of disclosure.

DSPAα1 so far is the best analyzed protease of this group. It has an amino acid sequence with a homology greater than 72% in comparison to the known human t-PA amino acid sequence (Krätzschmar et al, 1991). However, there are two essential differences between t-PA and DSPA. Firstly all DSPA has full protease activity as a single chain molecule, since it is—in contrast to t-PA—not converted into a double chain form (Gardell et al., 1989; Krätzschmar et al., 1991). Secondly, the catalytic activity of DSPA is near to being completely dependent on fibrin (Gardell et al., 1989; Bringmann et al., 1995; Toschie et al., 1998). For example the activity of DSPAα1 is increased 100,000 fold in the presence of fibrin whereas the t-PA activity is only increased 550 fold. In contrast, fibrinogen induces DSPA activity considerably less showing only a 7 to 9 fold increase (Bringmann et al., 1995). In conclusion, DSPA is considerably more dependent of fibrin and much more fibrin specific as wild type t-PA which is only activated 550-fold by fibrin.

Owing to its fibrinolytic properties and the high similarity to t-PA, DSPA is an interesting candidate for the development of a thrombolytic agent. However, the therapeutic use of DSPA as a thrombolytic agent has been limited to the treatment of myocardial infarction in the past. The reason for this limited application could be seen in role of t-PA in the glutamate induced neurotoxicity. No justified hopes existed, that a plasminogen activator which has a high similarity to t-PA could be used for a treatment of acute stroke with a reasonable hope of success.

Surprisingly it was shown that DSPA has no neurotoxic effects even though it shows a high resemblance (homology) to t-PA and even though the physiological effects of the molecules are comparable to those of t-PA to a large extent. The above unexpected finding led to the conclusion that DSPA after all may be successfully used as a thrombolytic agent for the therapy of stroke without causing severe risks of neuronal tissue damage. The fact, that DSPA can be used more than 3 hours after the onset of stroke symptoms makes it an extremely promising drug candidate.

A further teaching of the present invention that evolved from the above findings is the modification or production of further plasminogen activators in a way revealing the essential characteristics of DSPA, especially the lack of neurotoxicity. The basis for this teaching is the investigated relationship between structure and biochemical effects, making it possible to transform neurotoxic plasminogen activators into non-neurotoxic plasminogen activators and thereby to produce non-neurotoxic plasminogen activators on the basis of known or newly discovered neurotoxic plasminogen activators.

The new teaching is based on in vivo comparative studies of the neurodegenerative activity of t-PA and of DSPA which are performed by using the so called kainic acid model and a model for the examination of NMDA induced lesion of the striatum.

The kainic acid model (also kainic acid injury model) is based on the stimulation of the neurotoxic glutamate cascade by the external application of kainic acid (KA) as an agonist of the glutamate receptor of the kainic acid type (KA type) and of the NMDA and AMPA glutamate receptors. Using a t-PA deficient mouse stem as an experimental model it was possible to show that the sensitivity of the laboratory animals against kainic acid only reached the level of wild type mice after a supplementary application of external t-PA. In contrast, an infusion of an equimolar concentration of DSPA under the same experimental conditions does not restore the sensitivity to kainic acid (KA). It was concluded that the neurotoxic effect of t-PA was not induced by DSPA. A summary of these results is shown in table 2.

TABLE 2

| | | Hippocampal length intact (mm) | | |
|---|---|---|---|---|
| Treatment group | Number of animals | Contralateral side mean (SEM) | Ipsilateral side mean (SEM) | Percentage remaining |
| t-PA infusion (1.85 uM) + KA | 12 | 15.99 (0.208) | 3.63 (0.458) | 22.7* |
| DSPA infusion (1.85 uM) + KA | 11 | 16.07 (0.124) | 13.8 (0.579) | 85.87 |
| t-PA infusion (1.85 uM) + PBS | 3 | 16.75 (0.381) | 17.08 (0.363) | 101.97 |
| DSPA infusion (1.85 uM) + PBS | 3 | 15.75 (0.629) | 15.83 (0.363) | 100.50 |
| t-PA infusion (0.185 uM) + KA | 3 | 15.60 (0.702) | 5.07 (1.09) | 32.5 |
| DSPA infusion (18.5 uM) + KA | 3 | 16.06 (0.176) | 13.80 (1.22) | 85.93 |

*P < 0.0001

Figure 7:
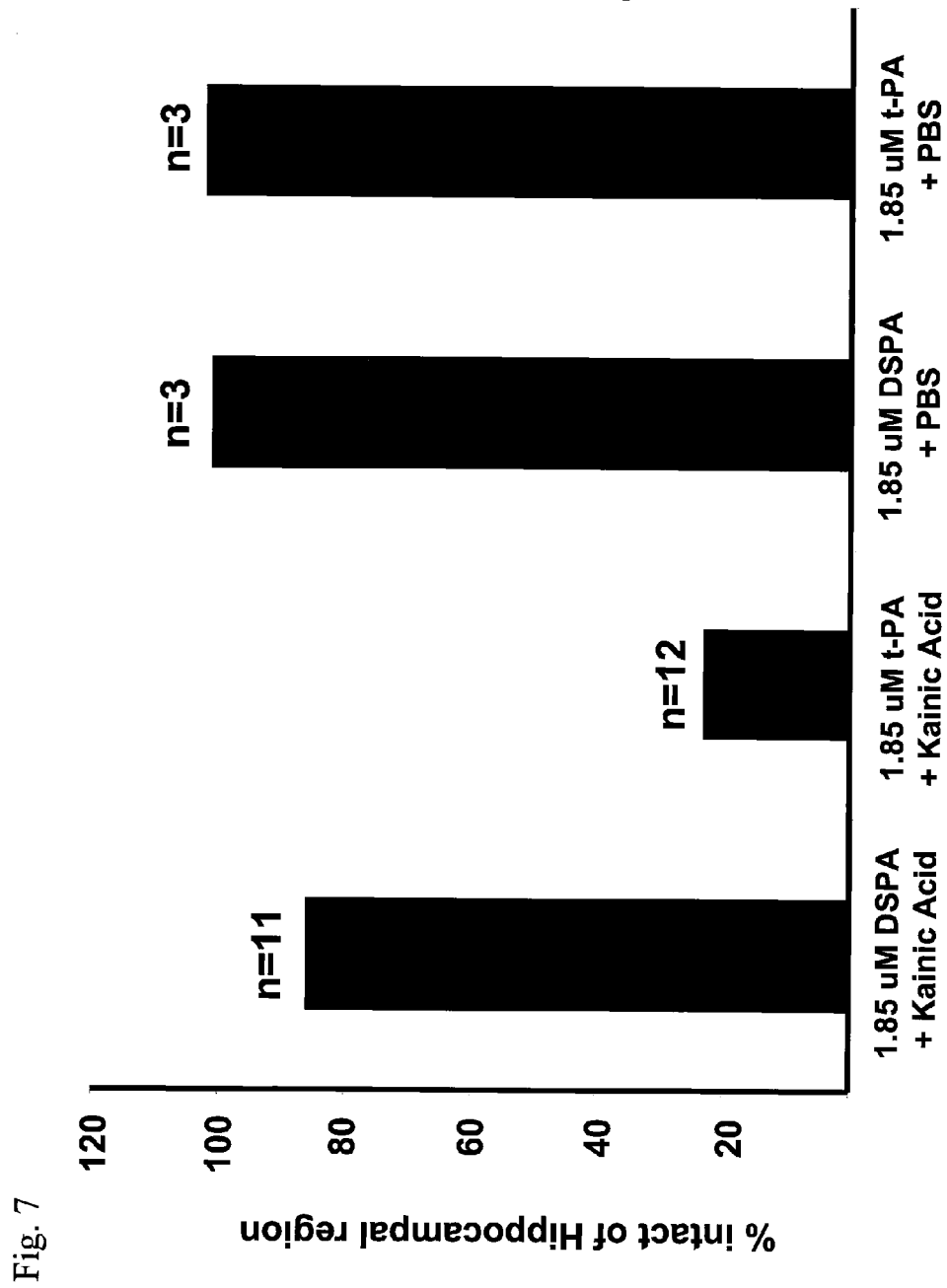
FIG. 7 shows results indicating that DSPA infused into t-PA −/− mice does not restore sensitivity to kainic acid-mediated neurodegeneration.
Figure 8:
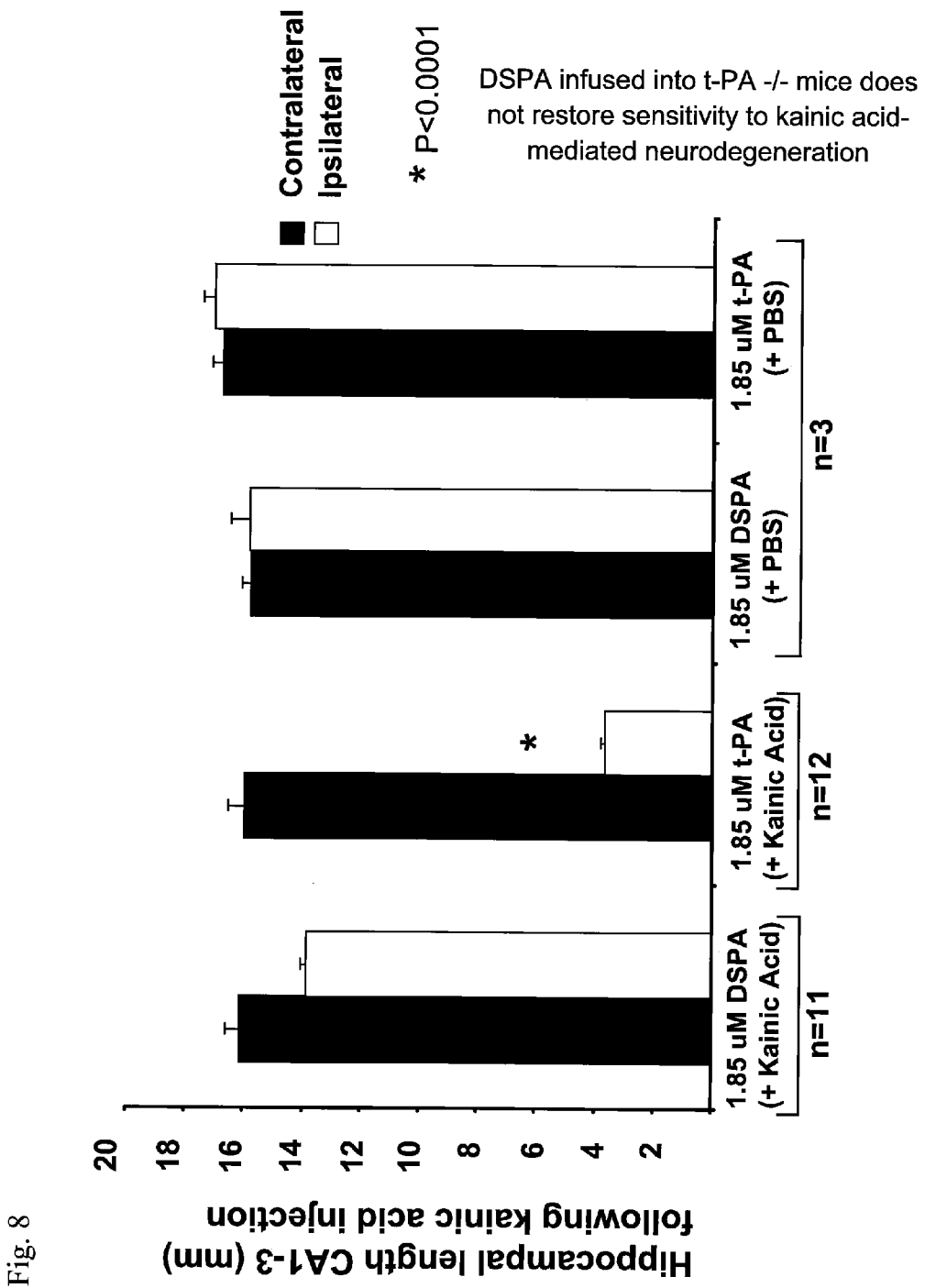
FIG. 8 also shows results indicating that DSPA infused into t-PA −/− mice does not restore sensitivity to kainic acid-mediated neurodegeneration.

Quantitative examinations based on this model revealed that even a 10-fold increase of the DSPA concentration could not restore the sensitivity of the t-PA deficient mice to the KA treatment whereas already a 10-fold lower t-PA concentration led to KA induced tissue damages. This leads to the conclusion that DSPA possesses an at least 100 fold lower neurotoxic potential as t-PA with respect to the stimulation of the neurodegeneration after KA treatment see also FIGS. 7 and 8.

In the second model of neurodegeneration, the possible effects of t-PA as well as DSPA on the stimulation of the NMDA dependent neurodegeneration were compared to wild type mice. For this purpose, NMDA (as an agonist of the glutamate receptor of the NMDA type) was injected in wild type mice alone or in combination with either t-PA or DSPA. This model allows the comparison of the effects of these proteases under conditions, which always lead to a neurodegeneration and to an influx of plasma proteins due to the breakdown of the blood brain barrier (Chen et al., 1999).

While working on this model the injection of NMDA led to reproducible lesions in the striatum of mice. The volume of lesions was increased by a combined injection of t-PA and NMDA by at least 50%. The co-injection with DSPA1 in contrast did not lead to an increase or extension of the lesions caused by NMDA. Even in the presence of plasma proteins which can freely diffuse in the region of the lesion induced by NMDA, DSPA did not result in an increase neurodegeneration (see also table 3).

TABLE 3

| Treatment group | Number of wild-type mice | Mean lesion volume (mm$^3$) (SEM) |
|---|---|---|
| NMDA alone | 8 | 1.85 (0.246) |
| NMDA + t-PA | 8 | 3.987 (0.293)* |
| NMDA + DSPA | 8 | 1.656 (0.094)** |

TABLE 3-continued

| Treatment group | Number of wild-type mice | Mean lesion volume (mm³) (SEM) |
|---|---|---|
| t-PA alone | 3 | 0.20 (0.011) |
| DSPA alone | 3 | 0.185 (0.016) |

*P < 0.0001
**Not significant

These results show that fibrin-free DSPA—in contrast to t-PA—behaves like an almost inert protease in the central nervous system of a mammal and also of a human—and therefore does not contribute to the neurotoxic effects caused by KA or NMDA. Despite of the prejudice against the therapeutic use of t-PA like proteins in stroke, this lack of neurotoxicity makes DSPA a suitable thrombolytic agent for the treatment of acute stroke.

First results of the clinical trials show the transferability of these results also for the treatment of stroke in humans. It was found that significant improvements can be achieved in patients after a successful perfusion (improvement by 8 points NIHSS or NIHSS score 0 to 1). Table 1 shows the data.

TABLE 1

| Patient | Baseline | NIHSS Post Tmt | Day 7 | Day 30 | Day 90 | sAEs |
|---|---|---|---|---|---|---|
| 1001 | 12 | 7 | 4 | 4 | * | Re-Infarction |
| 1002 | 8 | 9 | 2 | 0 | 0 | |
| 1003 | 8 | 10 | 12 | 10 | * | |
| 1004 | 8 | 4 | 2 | 0 | 0 | |
| 1005 | 11 | 11 | 4 | 5 | * | |
| 1006 | 9 | 7 | 1 | * | * | |
| 1007 | 14 | 6 | * | * | * | |
| 2001 | 19 | 20 | — | — | — | ICH, death |
| 2002 | 15 | 21 | — | — | — | ICH, death |
| 3001 | 8 | 7 | 6 | 5 | * | |
| 3002 | 15 | 16 | 9 | 8 | * | |
| 3003 | 10 | 19 | 21 | * | — | Death day 39 |

The lack of neurotoxicity of DSPA and of the other non-neurotoxic plasminogen activators (see above) offer the special advantage in stroke treatment that the use of these plasminogen activators—in contrast to the wild type t-PA—is not limited to a short maximum period of only 3 hours after the onset of stroke. In contrary, the treatment can be initiated later—for example after 6 hours or even later, since there is nearly no risk of stimulating excitotoxic responses. First clinical trials with DSPA prove a safe treatment of patients even in a time range of over 6 to 9 hours after the onset of stroke symptoms.

This option of a timely unlimited treatment with non-neurotoxic activators is of special importance, since it allows for the first time to treat patients with acute stroke symptoms safely even when diagnosis is delayed or the onset of the stroke cannot be determined with sufficient security. In the prior art, this group of patients was excluded from thrombolytic therapy with plasminogen activators due to unfavorable risk estimation. Consequently, an essential contra-indication for the authorized use of a thrombolytic agent for stroke is eliminated.

DSPA as well as further non-neurotoxic plasminogen activators show no tissue damaging side effects. However, it can be advantageous to apply them in combination with a neuroprotective agent for the treatment of stroke in order to limit the tissue damages induced by the glutamate occurring naturally in the human body. Neuroprotective agents inhibiting the glutamate receptor competitively or non-competitively can be used. Useful combinations are e.g. with the known inhibitors of the glutamate receptors of the NMDA type, the kainic acid type or the quisqualate type, as for example APV, APH, phencyclidine, MK-801, dextrorphane or cetamine.

Further a combination with cations can be advantageous since cations, especially Zn-ions, block the cation channel regulated by the glutamate receptor and can therefore reduce neurotoxic effects.

In a further advantageous embodiment, non-neurotoxic plasminogen activators can be combined with at least one further therapeutic agent or with a pharmaceutically tolerable carrier. The combination with a therapeutic agent which supports the reduction of tissue damage by vitalizing the cells is especially advantageous, since it contributes to the regeneration of already damaged tissue or serves for the prevention of further stroke incidents. Advantageous examples are combinations with antibiotics as quinones, anticoagulants as heparin or hirudin as well as with citicholine or acetylsalicylic acid.

A combination with at least one thrombin inhibitor can also be advantageous. Preferentially, thrombomodulin and thrombomodulin analogs like for example solulin, triabin or pallidipin can be used. Further combinations with anti-inflammatory substances are advantageous, since they influence the infiltration by leucocytes.

Comparing Examinations of t-PA and DSPA are Methods:
1. Animals

Wild-type mice (c57/Black 6) and t-PA deficient mice (t-PA −/− mice) (c57/Black 6) (Carmeliet et al., 1994) were supplied by Dr. Peter Carmeliet, Leuven, Belgium.
2. Protein Extraction from Brain Tissue The assessment of proteolytic activity in brain tissue following infusion of either t-PA or DSPA1 was performed by zymographic analysis (Granelli-Piperno and Reich, 1974). After an infusion over a period of seven days into the hippocampus, mice were anaesthetised, then transcardially perfused with PBS and the brains removed. The hippocampus region was removed, transferred to eppendorf tubes and incubated in an equal volume (w/v) (approx. 30-50 μm) of 0.5% NP-40 lysis buffer containing no protease inhibitors (0.5% NP-40, 10 mM Tris-HCl pH 7.4, 10 mM NaCL, 3 mM MgCl2, 1 mM EDTA). The brain extracts were homogenized by means of a hand-held glass homogeniser and left on ice for 30 minutes. The samples were then centrifuged and the supernatant was removed. The amount of proteins present was determined (Bio-Rad-reagent).
3. Zymographic Analysis of the Proteases The proteolytic activity in the samples and the brain tissue extracts was determined by zymographic analysis according to the method of Granelli, Piperno and Reich (1974). The samples with recombinant proteins (up to 100 nM) or the brain tissue extracts (20 μg) were subjected to a (10%) SDS-PAGE under non-reducing conditions. The gels were removed from the plates, washed in 1% triton X 100 for 2 hours and then overlaid onto an agarose gel containing polymerized fibrinogen and plasminogen (Granelli, Piperno and Reich, 1974). The gels were incubated at 37° C. in a humidified chamber until proteolysed zones appeared.
4. Intra-Hippocampal Infusion of t-PA, DSPA and Subsequent Injection of Kainic Acid The kainic acid injury model was based on studies of Tsirka et al. (1995). The animals were injected intraperitoneally (i.p.) with atropine (4 mg/kg) and then anaesthetised with an i.p. injection of sodium pentobarbitol (70 mg/kg). Afterwards mice were placed in a stereotaxic frame and a microosmotic pump (Alzet model 1007D, Alzet Calif. USA) containing 100 μl of either PBS or recombinant human t-PA (0.12 mg/ml, 1.85 µM) or DSPA1 (1.85 µM) was implanted subcutaneously between the shoulder blades. The pumps were connected via sterile tubes to a brain cannula and inserted through a burr opening made through the skull at coordinates bregma −2.5 mm, midiolateral 0.5 mm and dorsoventral 1.6 mm in order to introduce the liquid near the midline. The cannula was fixed at the desired position and the pumps were allowed to infuse the respective solutions at a rate of 0.5 µl per hour for a total of 7 days.

Two days after infusion of the proteases the mice were reanaesthetised and again placed in the stereotaxic frame. Afterwards 1.5 nmol of kainic acid (KA) in 0.3 µl PBS was injected unilaterally into the hippocampus. The coordinates were: bregma −2.5 mm, medial-lateral 1.7 mm and dorsoventral 1.6 mm. The excitotoxin (KA) was delivered for a duration of 30 seconds. After the kainic acid treatment the injection needle remained at these coordinates for further 2 minutes in order to prevent a reflux of the liquid.

5. Brain Processing Procedure

Five days after KA injection, the animals were anaesthetised and transcardially perfused with 30 ml PBS followed by 70 ml of a 4% paraformaldehyd solution, post fixed in the same fixative followed by incubation in 30% sucrose for further 24 hours. Coronal sections (40 µm) of the brain were then cut on a freezing microtome and either counter-stained with thionin (BDH, Australia) or processed for immunohistochemical examination as described below.

6. Quantification of Neuronal Loss within the Hippocampus

The quantification of neuronal loss in the CA1-CA3 hippocampal subfields was performed as previously described (Tsirka et al., 1995; Tsirka et al., 1996). Five consecutive parts of the dorsal hippocampus from all treatment groups were prepared taking care that the parts indeed comprised the place of the CA-injection and lesion area. The hippocampal subfields (CA1-CA3) of these sections were traced by means of camera lucida drawings of the hippocampus. The entire lengths of the subfields was measured by comparison to 1 mm standards traced under the same magnification. The lengths of tissue with viable pyramidal neurons (having normal morphology) and lengths of tissue devoid of neurons (no cells present, no thionin staining) was determined. The lengths, representing intact neurons and neuronal losses over each hippocampal subfield were averaged across sections and the standard deviations were determined.

7. Intra-Striatal NMDA Excitotoxic Lesions with or without t-PA or DSPA

Wild type mice (c57/Black 6) were anaesthetised and placed in a stereotaxic frame (see above). Mice then received an unilateral injection of 50 nmol NMDA in the left stratum, injected alone or in combination with either 46 µM rt-PA or 46 µM DSPA1. As controls t-PA and DSPA were also injected alone (both at a concentration of 46 µM). The injection coordinates were: bregma −0.4 mm, midiolateral 2.0 mm and dorsoventral 2.5 mm. The solutions (1 µl total volume for all treatments) were transferred over a period of 5 minutes at a rate of 0.2 µl/min and the needle was left in place for further 2 minutes after the injection in order to minimize the reflux of fluid. After 24 hours the mice were anaesthetised and perfused transcardially with 30 ml PBS followed by 70 ml of a 4% paraformaldehyd solution, post fixed in the same fixative for 24 hours with followed by incubation in 30% sucrose for further 24 hours. Brains were then cut (40 µm) on a freezing microtome and mounted onto gelatin coated glass slides.

8. Quantification of the Lesion Volume Following NMDA Injection

The quantification of the striatal lesion volume was performed using the method described by Callaway et al. (2000).

Ten consecutive coronal sections spanning the lesioned area were prepared. The lesioned area was visualised using the Callaway method and the lesion volume was quantified by the use of a micro computer imaging device (MCID, Imaging Research Inc., Brock University, Ontario, Canada).

9. Immunohistochemistry

Immunohistochemistry was performed using standard methodologies. Coronal sections were immersed in a solution of 3% $H_2O_2$ and 10% methanol for 5 minutes followed by an incubation in 5% normal goat serum for 60 minutes. The sections were incubated over night either with an anti-GFAP antibody (1:1,000; Dako, Carpinteria, Calif., USA) for the detection of astrocytes, with an anti-MAC-1 antibody (1:1,000; Serotec, Raleigh, N.C., USA) for the detection of microglia or with polyclonal anti-DSPA antibodies (Schering A G, Berlin). After rinsing, the sections were incubated with the appropriate biotinylated secondary antibodies (Vector Laboratories, Burlingame, Calif., USA). This was followed by a final incubation with avidin/biotin-complex (Vector Laboratories, Burlingame, Calif., USA) for 60 minutes before visualisation with 3,3'-diaminebebcidine/0.03% $H_2O_2$. Sections were then mounted on gelatin coated slides, dried, dehydrated and coverslipped with permount.

B. Results

1. Infusion of t-PA or DSPA Disperses into the Hippocampus of t-PA −/− Mice and Retains Proteolytic Activity The initial experiments were designed to confirm that both DSPA and t-PA retain their proteolytic activity for the 7 day period of the infusion. To this end, aliquots of t-PA and DSPA (100 nmol) were incubated at 37° C. and at 25° C. for 7 days in a water bath. In order to determine the proteolytic activity, 5 fold serial dilutions of the probes were subjected to SPS-PAGE under non-reducing conditions and proteolytic activity was assessed by zymographic analyses. An aliquot of t-PA and DSPA which had been kept frozen for a period of 7 days was used as a control. As can be seen in FIG. 1, there was only a minor loss of DSPA or t-PA activity at an incubation with either 25° C. or 37° C. over this period of time.

2. t-PA and DSPA Activity is Recovered in Hippocampal Extracts Prepared from t-PA −/− Mice Following Infusion First it had to be confirmed that the infused proteases were present in the brain of the infused animals and also retained their proteolytic activity while being in this compartment. To address this point, t-PA −/− were infused for seven days with either t-PA or DSPA (see above). Mice were then transcardially perfused with PBS and the brains removed. The ipsilateral and contralateral hippocampal regions were isolated as well as a region of the cerebellum (taken as a negative control). Tissue samples (20 µg) were subjected to SDS-PAGE and zymographic analysis according to the description in the methods section. As can be seen in FIG. 2, both t-PA and DSPA activities were detected in the ipsilateral region of the hippocampus, while some activity was also detected on the contralateral side. This indicates that the infused proteases not only retained their activity in the brain but had also diffused within the hippocampal region. As a control, no activity could be detected in the extract prepared from the cerebellum.

3. Immunohistochemical Assessment of DSPA

To further confirm that DSPA had indeed diffused into the hippocampal region, coronal brain sections of t-PA −/− mice were analysed immunohistochemically after DSPA infusion. DSPA-antigen was detected in the hippocampal region with the most prominent staining in the area of the infusion site. This result confirms that the infused DSPA is soluble and is indeed present in the hippocampus.

4. DSPA Infusion does not Restore Kainic-Acid Mediated Neurodegeneration In Vivo t-PA −/− mice are characteristically resistant to kainic acid (KA) mediated neurodegeneration. However, intrahippocampal infusion of rt-PA completely restores the sensitivity to KA-mediated injury. To determine whether DSPA could be substituted for t-PA in this model, t-PA −/− mice were infused intrahipocampically with either t-PA or DSPA using a mini-osmotic pump. For both groups 12 mice were tested. 2 days later the animals were injected with kainic acid and left to recover. 5 days later the animals were killed and the brains removed and prepared (see above). As controls, t-PA −/− mice were also infused with PBS prior to KA treatment (N=3).

Figure 3A:
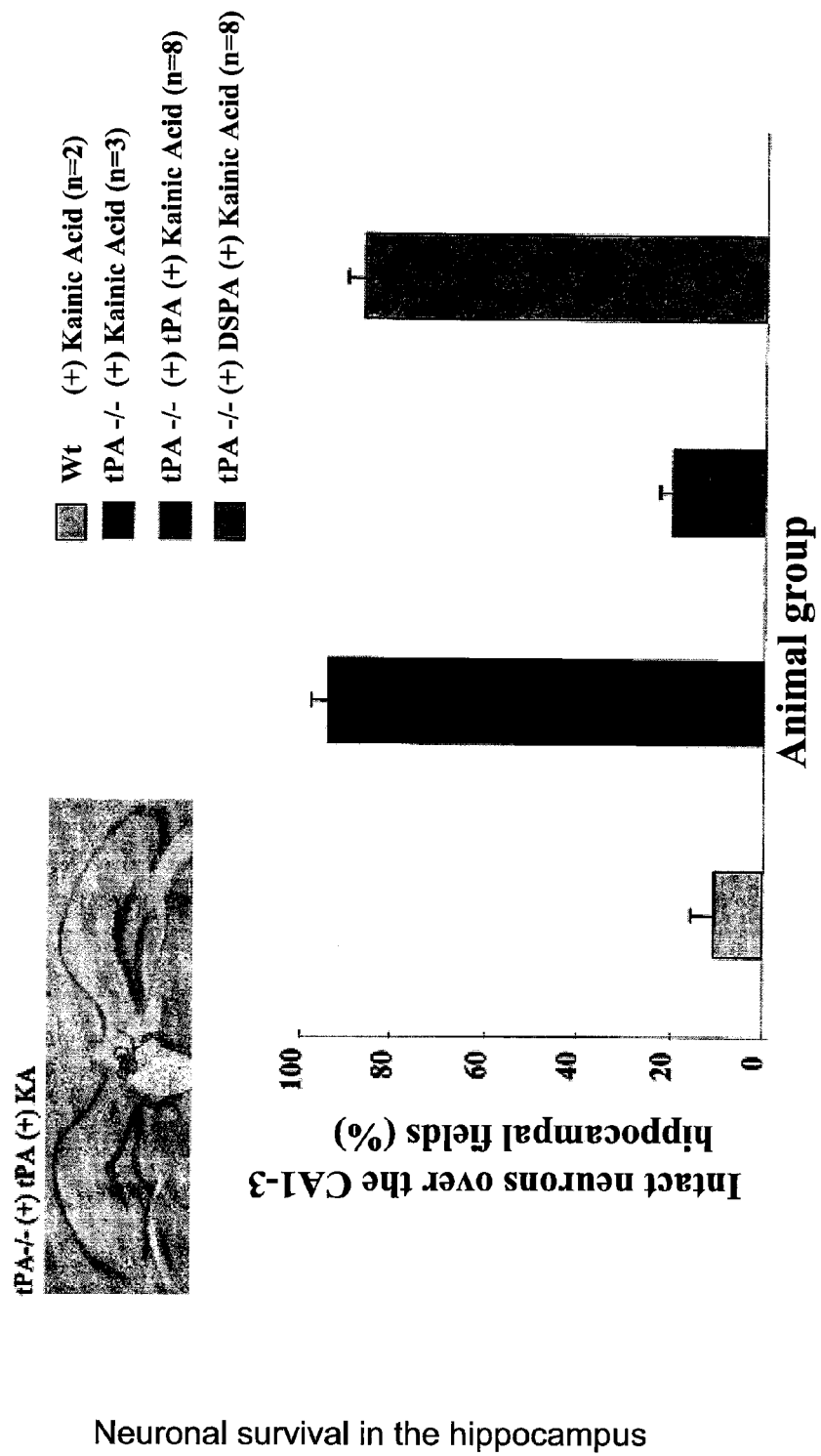
FIG. 3a shows neuronal survival in the hippocampus.
Figure 3B:
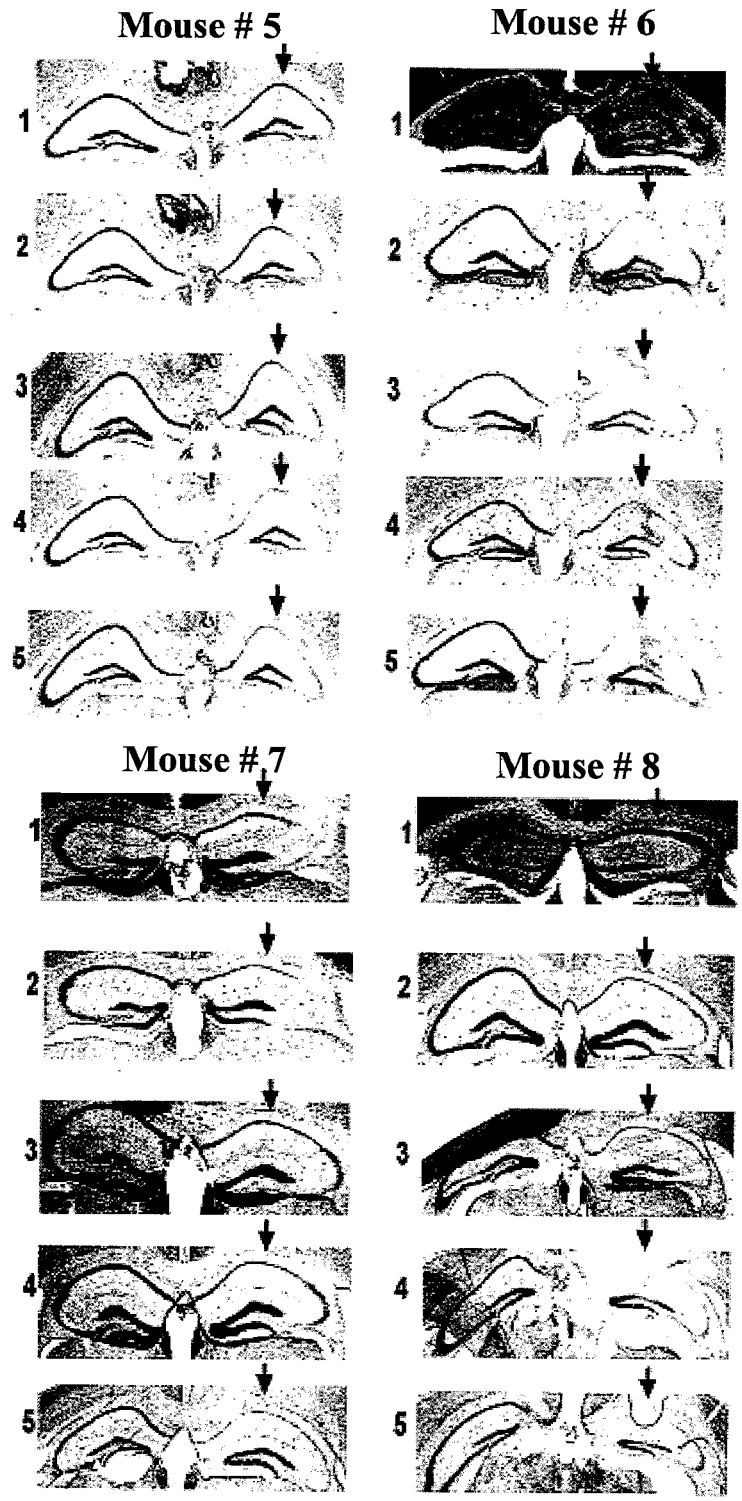
FIG. 3b shows serial sections of hippocampal regions for t-PA −/− mice infused with t-PA.

Coronal brain sections were prepared and the neurons detected by Nissl staining. As shown in FIG. 3, t-PA −/− mice infused with PBS were resistant to subsequent challenge with KA. However, infusion of recombinant t-PA restored sensitivity to KA treatment. In contrast, infusion of the same concentration of DSPA into the hippocampal region did not alter the sensitivity of the animals to KA.

A quantitation of those results was based on data obtained from 12 mice in each group. In 2 of the 12 mice infused with DSPA a small extent of neurodegeneration was observed. The reason for that is unclear and possibly not related to the presence of DSPA. The combined data consider this minor effect that was observed in the case of these 2 animals. All 12 mice treated with t-PA were sensitive against the KA treatment. These results show that in case of an infusion of t-PA or DSPA1 in equimolar concentrations only the administering of t-PA led to the restoration of sensitivity to KA induced neurodegeneration.

5. DSPA Infusion does not Result in Microglial Activation

The restoration of the KA sensitivity of the t-PA −/− mice caused by a t-PA infusion also results in a microglia activation (Rogove et al., 1999). To assess the degree of microglial activation following t-PA or DSPA infusion and subsequent KA treatment, coronal sections of mice were subjected to an immunohistochemical staining for activated microglia cells using the Mac-1 antibody. The restauration of KA sensitivity following t-PA infusion resulted in a clear increase in Mac-1 positive cells. This was not observed in mice infused with DSPA. Hence, the presence of DSPA does not result in the activation of microglia cells following KA treatment.

6. Titration of DSPA and t-PA in the Mice Hippocampus Region.

The concentration of t-PA used for the infusion was based on the concentration described by Tsirka et al. (1995) (100 µl of 0.12 mg/ml [1.85 µM]). The KA-injury experiments were repeated using a 10-fold lower of t-PA (0.185 µM) and a 10-fold higher amount of DSPA (18.5 µM). The lower t-PA concentration was still able to restore the sensitivity to KA treatment (n=3). Of special interest was the finding that the infusion of 10 fold increased DSPA concentration only caused a little neuronal loss following KA treatment. These data strongly point out that DSPA does not lead to an increase of sensitivity to KA.

7. Effect of t-PA and DSPA on NMDA-Dependent Neurodegeneration in Wild Type Mice The effects of t-PA and DSPA were also examined in a model of neurodegeneration in wild type mice. The injection of t-PA in the striatum of these mice provably led to an increase of the neurodegenerative effects caused by the glutamate analogue NMDA (Nicole et al., 2001).

NMDA was injected into the striatal region of wild type mice in the presence of t-PA or DSPA (each 46 µM) with a total volume of 1 µl. After 24 hours the brains were removed and the size of the lesions was quantified according to the Callaway method (Callaway et al., 2000) (see above). As can be seen in FIG. 4, injection of NMDA alone caused a reproducible lesion in all treated mice (N=4). When t-PA and NMDA were applied together, the size of the lesions was increased about 50% (P<0.01, n=4). In a clear contrast the co-injection of NMDA and the same concentration of DSPA did not lead to an increase in lesion size compared to NMDA alone Injection of t-PA or DSPA alone did not lead to a detectable neurodegeneration. The lack of effect of t-PA when being administered alone is consistent with the results of Nicole et al. (2001). These data show that the presence of DSPA does not increase neurodegeneration even during a neurodegenerative event.

In order to confirm that the injection of DSPA had indeed spread into the hippocampal region, immunohistochemistry was performed on coronal sections by use of the DSPA antibody. The examination showed that DSPA did indeed enter the striatal region.

Kinetic Analysis of the Plasminogen Activation by Indirect Chromogen Test

Indirect chromogen tests of the t-PA activity were performed using the substrate Lys-plasminogen (American Diagnostica) and spectrocyme PL (American Diagnostica) according to Madisan E. L., Goldsmith E. J., Gerard R. D., Gething M.-J., Sambrook J. F. (1989) Nature 339 721-724; Madison E. L O., Goldsmith E. J., Gething M. J., Sambrook J. F. and Bassel-Duby R. S. (1990) Proc. Nat. Acad. Sci. U.S.A 87, 3530-3533 as well as Madison E. L., Goldsmith E. J., Gething M. J., Sambrook J. F. and Gerard R. D. (1990) J. Biol. Chem. 265, 21423-21426. Tests were performed both in the presence and absence of the co-factor DESAFIB (American Diagnostica). DESAFIB is a preparation of soluble fibrin monomeres gained by the cleavage of highly pure human fibrinogen with the protease batroxobin. Batroxobin cleaves the $Arg^{16}$-$Gly^{17}$-binding in the A-chain of fibrinogen and thereby releases fibrinopeptid A. The resulting des-AA-fibrinogen representing fibrin I monomers is soluble in the absence of the peptide Gly-Pro-Arg-Pro. The concentration of Lys-plasminogen was varied from 0.0125 up to 0.2 µM in the presence of DESAFIB and from 0.9 to 16 µM in absence of the co-factor.

Indirect Chromogen Tests in the Presence of Different Stimuli.

Indirect chromogen standard tests were performed according to the publications cited above. Probes of 100 µl total volume containing 0.25-1 ng enzyme, 0.2 µM Lys-plasminogen and 0.62 mM spectrocyme PL were used. The tests were performed either in the presence of buffer, 25 µg/ml DESAFIB, 100 µg/ml cyanogen bromide fragments of fibrinogen (American Diagnostica) or 100 µg/ml of the stimulatory 13 amino acid peptide P368. The analysis were performed in microtiter-plates and the optic density was determined at a wave length of 405 nm every 30 seconds for 1 hour in a "Molecular Devices Thermomax". The reaction temperature was 37° C.

The complete disclosure of all patents, patent documents and publications cited herein are incorporated by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

What is claimed is:

1. A method of treating ischemic stroke in a human in need thereof, comprising administering intravenously to the human a therapeutically effective amount of recombinantly produced *Desmodus rotundus* Salivary Plasminogen Activator alpha 1 (DSPAα1);
   wherein the administration of DSPAα1 has reduced glutamate mediated neurotoxic effects compared to tissue plasminogen activator (t-PA) such that the DSPAα1 can be administered more than 3 hours after onset of stroke symptoms; and
   wherein the DSPAα1 is not administered in combination with an anti-inflammatory substance or in combination with an anti-coagulant substance.

2. The method according to claim 1, wherein the DSPAα1 is administered to the human within 6 hours after onset of stroke symptoms.

3. The method according to claim 1, wherein the DSPAα1 is administered to the human within 9 hours after onset of stroke symptoms.

4. The method according to claim 1, wherein the DSPAα1 is administered to the human 6 to 9 hours after onset of stroke symptoms.

5. The method according to claim 1, wherein the DSPAα1 is administered to the human 3 to 9 hours after onset of stroke symptoms.

6. The method according to claim 1, wherein the DSPAα1 is administered to the human 3 to 6 hours after onset of stroke symptoms.

* * * * *

SEQUENCE LISTING

<160> NUMBER OF SEQ ID NOS: 2

<210> SEQ ID NO 1
<211> LENGTH: 476
<212> TYPE: PRT
<213> ORGANISM: Artificial Sequence
<220> FEATURE:
<223> OTHER INFORMATION: A modified tissue plasminogen activator.

<400> SEQUENCE: 1

```
Met Val Asn Thr Met Lys Thr Lys Leu Leu Cys Val Leu Leu Leu Cys
 1               5                  10                  15

Gly Ala Val Phe Ser Leu Pro Arg Gln Glu Thr Tyr Arg Gln Leu Ala
            20                  25                  30

Arg Gly Ser Arg Ala Tyr Gly Val Ala Cys Lys Asp Glu Ile Thr Gln
        35                  40                  45

Met Thr Tyr Arg Arg Gln Glu Ser Trp Leu Arg Pro Glu Val Arg Ser
    50                  55                  60

Lys Arg Val Glu His Cys Gln Cys Asp Arg Gly Gln Ala Arg Cys His
65                  70                  75                  80

Thr Val Pro Val Lys Ser Cys Ser Glu Pro Arg Cys Phe Asn Gly Gly
                85                  90                  95

Thr Cys Gln Gln Ala Leu Tyr Phe Ser Asp Phe Val Cys Gln Cys Pro
            100                 105                 110

Glu Gly Phe Ala Gly Lys Cys Cys Glu Ile Asp Thr Arg Ala Thr Cys
        115                 120                 125

Tyr Glu Asp Gln Gly Ile Ser Tyr Arg Gly Thr Trp Ser Thr Ala Glu
    130                 135                 140

Ser Gly Ala Glu Cys Thr Asn Trp Asn Ser Ser Ala Leu Ala Gln Lys
145                 150                 155                 160

Pro Tyr Ser Gly Arg Arg Pro Asp Ala Ile Arg Leu Gly Leu Gly Asn
                165                 170                 175

His Asn Tyr Cys Arg Asn Pro Asp Arg Asp Ser Lys Pro Trp Cys Tyr
            180                 185                 190

Val Phe Lys Ala Gly Lys Tyr Ser Ser Glu Phe Cys Ser Thr Pro Ala
        195                 200                 205

Cys Ser Ser Thr Cys Gly Leu Arg Gln Tyr Ser Gln Pro Gln Phe His
    210                 215                 220

Ser Thr Gly Gly Leu Phe Ala Asp Ile Ala Ser His Pro Trp Gln Ala
225                 230                 235                 240

Ala Ile Phe Ala Lys His Arg Arg Ser Pro Gly Glu Arg Phe Leu Cys
                245                 250                 255

Gly Gly Ile Leu Ile Ser Ser Cys Trp Ile Leu Ser Ala Ala His Cys
            260                 265                 270

Phe Gln Glu Arg Phe Pro Pro His His Leu Thr Val Ile Leu Gly Arg
        275                 280                 285

Thr Tyr Arg Val Val Pro Gly Glu Glu Gln Lys Phe Glu Val Glu
    290                 295                 300

Lys Tyr Ile Val His Lys Glu Phe Asp Asp Thr Tyr Asp Asn Asp
305                 310                 315                 320

Ile Ala Leu Leu Gln Leu Lys Ser Asp Ser Arg Cys Ala Gln Glu
                325                 330                 335

Ser Ser Val Val Arg Thr Val Cys Leu Pro Pro Ala Asp Leu Gln Leu
            340                 345                 350
```

-continued

```
Pro Asp Trp Thr Glu Cys Glu Leu Ser Gly Tyr Gly Lys His Glu Ala
            355                 360                 365

Leu Ser Pro Phe Tyr Ser Glu Arg Leu Lys Glu Ala His Val Arg Leu
        370                 375                 380

Tyr Pro Ser Ser Arg Cys Thr Ser Gln His Leu Leu Asn Arg Thr Val
385                 390                 395                 400

Thr Asp Asn Met Leu Cys Ala Gly Asp Thr Arg Ser Gly Gly Pro Gln
                405                 410                 415

Ala Asn Leu His Asp Ala Cys Gln Gly Asp Ser Gly Gly Pro Leu Val
            420                 425                 430

Cys Leu Asn Asp Gly Arg Met Thr Leu Val Gly Ile Ile Ser Trp Gly
            435                 440                 445

Leu Gly Cys Gly Gln Lys Asp Val Pro Gly Val Tyr Thr Lys Val Thr
450                 455                 460

Asn Tyr Leu Asp Trp Ile Arg Asp Asn Met Arg Pro
465                 470                 475

<210> SEQ ID NO 2
<211> LENGTH: 477
<212> TYPE: PRT
<213> ORGANISM: Artificial Sequence
<220> FEATURE:
<223> OTHER INFORMATION: A modified urokinase.

<400> SEQUENCE: 2

Met Val Asn Thr Met Lys Thr Lys Leu Leu Cys Val Leu Leu Leu Cys
1               5                   10                  15

Gly Ala Val Phe Ser Leu Pro Arg Gln Glu Thr Tyr Arg Gln Leu Ala
                20                  25                  30

Arg Gly Ser Arg Ala Tyr Gly Val Ala Cys Lys Asp Glu Ile Thr Gln
            35                  40                  45

Met Thr Tyr Arg Arg Gln Glu Ser Trp Leu Arg Pro Glu Val Arg Ser
        50                  55                  60

Lys Arg Val Glu His Cys Gln Cys Asp Arg Gly Ser Asn Glu Leu His
65                  70                  75                  80

Gln Val Pro Ser Asn Ser Cys Asp Glu Pro Arg Cys Leu Asn Gly Gly
                85                  90                  95

Thr Cys Val Ser Asn Lys Tyr Phe Ser Ile His Trp Cys Asn Cys Pro
            100                 105                 110

Lys Lys Phe Gly Gly Gln His Cys Glu Ile Asp Lys Ser Lys Thr Cys
        115                 120                 125

Tyr Glu Gly Asn Gly His Phe Tyr Arg Gly Lys Ala Ser Thr Asp Thr
    130                 135                 140

Met Gly Arg Pro Cys Leu Pro Trp Asn Ser Ala Thr Val Leu Gln Gln
145                 150                 155                 160

Thr Tyr His Ala His Arg Ser Asp Ala Leu Gln Leu Gly Leu Gly Lys
                165                 170                 175

His Asn Tyr Cys Arg Asn Pro Asp Asn Arg Arg Arg Pro Trp Cys Tyr
            180                 185                 190

Val Gln Val Gly Leu Lys Pro Leu Val Gln Glu Cys Met Val His Asp
        195                 200                 205

Cys Ala Asp Phe Gln Cys Gly Gln Lys Thr Leu Arg Glu Pro Arg Phe
    210                 215                 220

His Ser Thr Gly Gly Glu Phe Thr Thr Ile Glu Asn Gln Pro Trp Phe
225                 230                 235                 240

Ala Ala Ile Tyr Arg Arg His Arg Gly Gly Ser Gly Val Thr Tyr Val
```

-continued

```
                     245                    250                    255
Cys Gly Gly Ser Leu Met Ser Pro Cys Trp Val Ile Ser Ala Thr His
            260                    265                    270

Cys Phe Ile Asp Tyr Pro Lys Lys Glu Asp Tyr Ile Val Tyr Leu Gly
            275                    280                    285

Arg Ser Arg Leu Asn Ser Asn Thr Gln Gly Glu Met Lys Phe Glu Val
            290                    295                    300

Glu Asn Leu Ile Leu His Lys Asp Tyr Ser Ala Asp Thr His His Asn
305                     310                    315                    320

Asp Ile Ala Leu Leu Lys Ile Arg Ser Lys Glu Gly Arg Cys Ala Gln
                    325                    330                    335

Pro Ser Arg Thr Ile Gln Thr Ile Cys Leu Pro Ser Met Tyr Asn Asp
            340                    345                    350

Pro Gln Phe Gly Thr Ser Cys Glu Ile Thr Gly Phe Gly Lys Glu Asn
            355                    360                    365

Ser Thr Asp Tyr Leu Tyr Pro Glu Gln Leu Lys Met Thr Val Val Lys
    370                    375                    380

Leu Ile Ser His Arg Glu Cys Gln Gln Pro His Tyr Tyr Gly Ser Glu
385                     390                    395                    400

Val Thr Thr Lys Met Leu Cys Ala Ala Asp Pro Gln Trp Lys Glu Ile
                    405                    410                    415

Tyr Pro Asn Val Thr Asp Ser Cys Gln Gly Asp Ser Gly Gly Pro Leu
            420                    425                    430

Val Cys Ser Leu Gln Gly Arg Met Thr Leu Thr Gly Ile Val Ser Trp
            435                    440                    445

Gly Arg Gly Cys Ala Leu Lys Asp Lys Pro Gly Val Tyr Thr Arg Val
    450                    455                    460

Ser His Phe Leu Pro Trp Ile Arg Ser His Thr Lys Leu
465                     470                    475
```